(12) United States Patent
Frost et al.

(10) Patent No.: US 7,977,077 B2
(45) Date of Patent: Jul. 12, 2011

(54) SYNTHESIS OF INTERMEDIATES OF OSELTAMIVIR CARBOXYLATES

(75) Inventors: John W. Frost, Okemos, MI (US); Jiantao Guo, Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 997 days.

(21) Appl. No.: 11/700,238

(22) Filed: Jan. 30, 2007

(65) Prior Publication Data

US 2007/0190621 A1      Aug. 16, 2007

Related U.S. Application Data

(60) Provisional application No. 60/763,484, filed on Jan. 30, 2006, provisional application No. 60/763,485, filed on Jan. 30, 2006.

(51) Int. Cl.
*C12P 7/22* (2006.01)
*C12N 15/00* (2006.01)
*C12N 1/21* (2006.01)
*C07H 21/00* (2006.01)
*C12P 21/00* (2006.01)
*C07K 14/00* (2006.01)
*C12N 9/04* (2006.01)
*C12N 9/10* (2006.01)
*C12N 9/12* (2006.01)
*C12N 9/16* (2006.01)
*C12N 9/88* (2006.01)
*C12N 9/90* (2006.01)

(52) U.S. Cl. ............... 435/156; 435/146; 435/320.1; 435/69.1; 435/252.3; 435/252.33; 435/410; 435/254.11; 435/190; 435/193; 435/233; 435/232; 435/196; 435/194; 536/23.2; 530/350

(58) Field of Classification Search .................. 435/156, 435/146, 320.1, 69.1, 252.3, 252.33, 410, 435/254.11, 190, 193, 233, 232, 196, 194; 530/350; 536/23.2
See application file for complete search history.

(56) References Cited

U.S. PATENT DOCUMENTS

| | | |
|---|---|---|
| 5,168,056 A | 12/1992 | Frost |
| 5,798,236 A | 8/1998 | Frost et al. |
| 6,403,824 B2 | 6/2002 | Abrecht et al. |
| 6,462,226 B1 | 10/2002 | Mair |
| 6,472,169 B1 | 10/2002 | Frost et al. |
| 6,613,552 B1 | 9/2003 | Frost et al. |

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Inaoka et al., The Journal of Biological Chemistry 279(5):3885-3892, 2004.*
Kooistra et al., GenBank accession No. Y14081, Jan. 1999.*
Guo et al., Organic Letters 6(10):1585-1588, 2004.*
Bradley, Star role for bacteria in controlling flu pandemic?, Nature Reviews Drug Discovery 4(12):945 (2005).
Brown et al., Transport and Utilization of the Biosynthetic Intermediate Shikimic Acid in *Escherichia coli*, Biochimica et Biophysics Acta, 428:550-562 (1976).
Chen et al., Biosynthesis of ansatrienin (mycotrienin) and naphthomycin; Identification and analysis of two separate biosynthesis gene clusters in *Streptomyces collinus* Tu 1892, Eur: J. Biochem., 261:98-107 (1999).
Cox, Biosynthesis, Annu. Rep. Prog. Chem., Sect. B, Organic Chemistry, 94:187-206 (1998).
Dell et al., Identification and Removal of Impediments to Biocatalytic Synthesis of Aromatics from D-Glucose: Rate-Limiting Enzymes in the Common Pathway of Aromatic Amino Acid Biosynthesis, J. Am. Chem. Soc., 115(24):11581-11589 (1993).
Draths et al., Biocatalysis and Nineteenth Century Organic Chemistry: Conversion of DGlucose into Quinoid Organics, J. Am. Chem. Soc., 114(24):9726 (1992).
Draths et al., Environmentally Compatible Synthesis of Catechol from D-Glucose, J. Am. Chem. Soc., 117(9):2395-2400 (1995).
Frost et al., Biocatalytic Syntheses of Aromatics from D-Glucos: Renewable Microbial Sources of Aromatic Compounds, Annu. Rev. Microbiol., 49:557-79 (1995).
Frost et al., Dehydroquinate Synthase from *Escherichia coli*: Purification, Cloning, and Construction of Overproducers of the Enzyme, Biochemistry, 23:4470-4475 (1984).
Guo et al., Biosynthesis of 1-Deoxy-1-imino-D-erythrose 4-Phosphate: A Defining Metabolite in the Aminoshikimate Pathway, J. Am. Chem. Soc., 124(4):528-529 (2002).
Guo et al., Kanosamine Biosynthesis: A Likely Source of the Aminoshikimate Pathway's Nitrogen Atom, J. Am. Chem. Soc., 124(36):10642-10643 (2002).
Guo et al., Synthesis of Aminoshikimic Acid, Org. Lett., 6(10):1585-1588 (2004).
Kim et al., Influenza Neuraminidase Inhibitors Possessing a Novel Hydrophobic Interaction in the Enzyme Active Site: Design, Synthesis, and Structural Analysis of Carbocyclic Sialic Acid Analogues with Potent Anti-Influenza Activity, J. Am. Chem. Soc., 119:681-690 (1997).
Mitsuhashi et al., Aromatic Biosynthesis. XIII. Conversion of Quinic Acid to 5-Dehydroquinic Acid by Quinic Dehydrogenase, Biochim. Biophys. Acta, 15:268-280 (1954).
Pittard et al., Gene Controlling the Uptake of Shikimic Acid by *Escherichia coli*, J. Bacteriol., 92(4):1070-1075 (1966).
Roche, Tamiflu (oseltamivir phosphate) Capsules and for Oral Suspension, Roche Pharmaceuticals, 1-17 (2004).
Rohloff et al., Practical Total Synthesis of the Anti-Influenza Drug GS-4104, J. Org. Chem., 63(12):4545-4550 (1998).

(Continued)

*Primary Examiner* — Delia M Ramirez
(74) *Attorney, Agent, or Firm* — Greenberg Traurig, LLP; Jennifer A. Camacho; Fang Xie

(57) ABSTRACT

Enzymatic pathways for production of aminoshikimate, kanosamine, intermediates, and derivatives thereof; nucleic acid encoding and cells containing the enzymes; compositions containing aminoshikimate, kanosamine, an intermediate or derivative thereof; and use of the cells and pathways for biosynthetic production of aminoshikimate, kanosamine, intermediates, and derivatives thereof.

39 Claims, 4 Drawing Sheets

OTHER PUBLICATIONS

Weaver et al., Cloning of an aroF Allele Encoding a Tyrosine-Insensitive 3-Deoxy-D-arabino-Heptulosonate 7-Phosphate Synthase, Journal of Bacteriology, 172(11):6581-6584 (1990).

Yarnell, Complexity of Tamiflu Manufacturing May Hamper On Demand Production, Chemical & Engineering News, 83(35):22 (2005).

Dell et al., Identification and Removal of Impediments to Biocatalytic Synthesis of Aromatics from D-Glucose: Rate-Limiting Enzymes in the Common Pathway of Aromatic Amino Acid Biosynthesis, J. Am. Chem. Soc., 115(24):11581-11589 (1993).

\* cited by examiner

SEQUENCE LISTING

```
<160> NUMBER OF SEQ ID NOS: 20

<210> SEQ ID NO 1
<211> LENGTH: 1053
<212> TYPE: DNA
<213> ORGANISM: Bacillus subtilis
<220> FEATURE:
<221> NAME/KEY: misc_feature
<222> LOCATION: (1)..(1053)
<223> OTHER INFORMATION: Coding sequence for 3-keto-D-glucose-6-
      phosphate (3KG6P) dehydrogenase (YhjJ) from Genbank Accession No.
      Z99109

<400> SEQUENCE: 1
atgaagaaga taggcatcat aggtgcaggt ggtattgcaa gagcgcatgc aactgcttta        60
tctacaataa aaaatgcaga gttagtaggg gtatatgaca taaatcaaca aaatgcggaa       120
agctttgtga aaactttcgg cgggaagtca tttgaaaacg tagatgaact aattgatgcc       180
tcagaaggtt taattgtagc atcaccaaac ttttgccata agaacatgc tttgcaagca        240 ttaggaaaac ataagcatgt attatgtgaa aagcctatgg ctatttctct tgaagaagca       300
agcataatga aagatactgc tgaaaggttg agcgtaagag ccagtatggg atttaattat       360
agatatttat cttacgtaaa tatcttaaaa agcttaatta tcaataatga actaggtaac       420
atactgtcca taaaagtaca cttcaagaaa aatagtgcac ttagacgtaa gaagtttact       480
tggagagatg acgctaatag taagaagacg agtggatcat tggggggatct gggtattcac       540 cttattgaca tggtatggta tttgttcgag agtgatttca tcacagaatc agtaagggca       600
```

-continued

```
aagatgaaca caaatgtaaa aacaaaagag gataaacagg tacttgtaga tgactatgca      660
gaaatttatg gccagctgag gaacaaggta tttgtaaata tcatcacatc aaagtgttct      720
gtacctgaag actgtggttt tagcattgag gtagttggac acaaaaaaga gtttaaatac      780
cacacaggta atcctcacgt ttacaagctc atagatggct tgaacgtggt agactgccca      840
gtaccgcaaa gcctattaaa cgatccgcca acgagtttt atggatgggc tgattctttt      900
agaagcgagt taatcaattg gattgcatca actcagaatg attgggttga gatcccttct      960
tttagtgatg gttttagatc tcaggaagta ttagaaatgt tctttgagaa agacagcaac     1020
tctcaaccca tgtctgtttc agcagtcaac tag                                   1053
```

<210> SEQ ID NO 2
<211> LENGTH: 350
<212> TYPE: PRT
<213> ORGANISM: Bacillus subtilis
<220> FEATURE:
<221> NAME/KEY: MISC_FEATURE
<222> LOCATION: (1)..(350)
<223> OTHER INFORMATION: 3-keto-D-glucose-6-phosphate (3KG6P)
      dehydrogenase (YhjJ) from Genbank Accession No. CAB12893

<400> SEQUENCE: 2

```
Met Lys Lys Ile Gly Ile Ile Gly Ala Gly Gly Ile Ala Arg Ala His
1               5                   10                  15

Ala Thr Ala Leu Ser Thr Ile Lys Asn Ala Glu Leu Val Gly Val Tyr
            20                  25                  30

Asp Ile Asn Gln Gln Asn Ala Glu Ser Phe Val Lys Thr Phe Gly Gly
        35                  40                  45

Lys Ser Phe Glu Asn Val Asp Glu Leu Ile Asp Ala Ser Glu Gly Leu
    50                  55                  60

Ile Val Ala Ser Pro Asn Phe Cys His Lys Glu His Ala Leu Gln Ala
65                  70                  75                  80

Leu Gly Lys His Lys His Val Leu Cys Glu Lys Pro Met Ala Ile Ser
                85                  90                  95

Leu Glu Glu Ala Ser Ile Met Lys Asp Thr Ala Glu Arg Leu Ser Val
            100                 105                 110

Arg Ala Ser Met Gly Phe Asn Tyr Arg Tyr Leu Ser Tyr Val Asn Ile
        115                 120                 125

Leu Lys Ser Leu Ile Ile Asn Asn Glu Leu Gly Asn Ile Leu Ser Ile
    130                 135                 140

Lys Val His Phe Lys Lys Asn Ser Ala Leu Arg Arg Lys Lys Phe Thr
145                 150                 155                 160

Trp Arg Asp Asp Ala Asn Ser Lys Lys Thr Ser Gly Ser Leu Gly Asp
                165                 170                 175

Leu Gly Ile His Leu Ile Asp Met Val Trp Tyr Leu Phe Glu Ser Asp
            180                 185                 190

Phe Ile Thr Glu Ser Val Arg Ala Lys Met Asn Thr Asn Val Lys Thr
        195                 200                 205

Lys Glu Asp Lys Gln Val Leu Val Asp Asp Tyr Ala Glu Ile Tyr Gly
    210                 215                 220

Gln Leu Arg Asn Lys Val Phe Val Asn Ile Ile Thr Ser Lys Cys Ser
225                 230                 235                 240

Val Pro Glu Asp Cys Gly Phe Ser Ile Glu Val Val Gly His Lys Lys
                245                 250                 255

Glu Phe Lys Tyr His Thr Gly Asn Pro His Val Tyr Lys Leu Ile Asp
            260                 265                 270
```

```
Gly Leu Asn Val Val Asp Cys Pro Val Pro Gln Ser Leu Leu Asn Asp
            275                 280                 285

Pro Pro Asn Glu Phe Tyr Gly Trp Ala Asp Ser Phe Arg Ser Glu Leu
        290                 295                 300

Ile Asn Trp Ile Ala Ser Thr Gln Asn Asp Trp Val Glu Ile Pro Ser
305                 310                 315                 320

Phe Ser Asp Gly Phe Arg Ser Gln Glu Val Leu Glu Met Phe Phe Glu
                325                 330                 335

Lys Asp Ser Asn Ser Gln Pro Met Ser Val Ser Ala Val Asn
                340                 345                 350

<210> SEQ ID NO 3
<211> LENGTH: 1326
<212> TYPE: DNA
<213> ORGANISM: Bacillus subtilis
<220> FEATURE:
<221> NAME/KEY: misc_feature
<222> LOCATION: (1)..(1326)
<223> OTHER INFORMATION: Coding sequence for 3-keto-D-glucose-6-
      phosphate (3KG6P) transaminase (YhjL) from Genbank Accession No.
      Z99109

<400> SEQUENCE: 3
atgcaaaaac aggttaagat ttcaggtaaa agcaaagaaa acatgtcact attaaaacac      60
ttaaaaggtg acgtacaagg aaaagaactt gttattgaag acagtattgt aaacgagcgg     120
tggaaacaag tattaaaaga aaagatagat attgaacatg accttttcaa ctatcaaaaa     180
aatcgtgaaa tcagtaaagt cccttttttg cctgtagaca gattaataac caatgatgaa     240
gtggaagata tcttaaatac attaactgaa gttttgccaa ctggaaaatt tacgagtggt     300
ccctatttag agcaattcga aaagttttta tctacatatt tacataaaag gtatgtaatt     360
gcaaccagca gtggaaccga tgctatatg ataggtttat tggctttagg gttaaaccca     420
ggggatgaag ttatcatgcc ggctaatagc ttttcagcta ctgaaaatgc tgtgttagct     480
tcgggaggcg ttcctatcta tgtagatatt aacccacaaa cattctgcat cgatcctgac     540
aaaattgaag aagcaataac tcctatacaa agtttattc tacctgtgca tttatacgga     600
aaacattcag acatgcagca tatccgtcaa atcgcaaatc gttataaatt aaaagtaatt     660
gaagatgcct gccaaggaat tggactgaca gacttaggaa agtatgcaga catcactaca     720 ttaagttta tcccctataa gaattttggt gtatgtggca aggctggggc aatagcaact     780
gataatgaag aactcgctaa aaatgcatt caatttagtt atcacggttt tgaagtaaat     840
gtaaaaaata agaaagtcat caattttgga tttaattcaa aaatggacaa tttacaggca     900
gcaattggtt tagagagaat gaagtacctt tcattaaaca acttcaaaag attgttcttg     960
gcggatagat acattaccca attagcagag ttgcagaata aaggctatat tgaattacca    1020
gaattaagtg aagatcatgt atggcatctg tttcctatta aggtaagaac agaagatagg    1080
gcagatatca tgactaaatt aaatgaagat tttggtgttc aaacagatgt atattatcca    1140
atactttctc atatgcaaaa aactcccttta gtacaggaca agtatgcagg actccaattg    1200
gttcatacgg aaaaggctca tagtcaggta ctgcatttgc ctttatatcc gtcatttact    1260
ttagaagaac aagacagagt aatggaggga ctgtttcatg ttattaagca agaaatcgga    1320
gtataa                                                              1326

<210> SEQ ID NO 4
<211> LENGTH: 441
<212> TYPE: PRT
```

```
<213> ORGANISM: Bacillus subtilis
<220> FEATURE:
<221> NAME/KEY: MISC_FEATURE
<222> LOCATION: (1)..(441)
<223> OTHER INFORMATION: 3-keto-D-glucose-6-phosphate (3KG6P)
      transaminase (YhjL) from Genbank Accession No. CAB12895

<400> SEQUENCE: 4

Met Gln Lys Gln Val Lys Ile Ser Gly Lys Ser Lys Glu Asn Met Ser
1               5                   10                  15

Leu Leu Lys His Leu Lys Gly Asp Val Gln Gly Lys Glu Leu Val Ile
                20                  25                  30

Glu Asp Ser Ile Val Asn Glu Arg Trp Lys Gln Val Leu Lys Glu Lys
            35                  40                  45

Ile Asp Ile Glu His Asp Leu Phe Asn Tyr Gln Lys Asn Arg Glu Ile
        50                  55                  60

Ser Lys Val Pro Phe Leu Pro Val Asp Arg Leu Ile Thr Asn Asp Glu
65                  70                  75                  80

Val Glu Asp Ile Leu Asn Thr Leu Thr Glu Val Leu Pro Thr Gly Lys
                85                  90                  95

Phe Thr Ser Gly Pro Tyr Leu Glu Gln Phe Glu Lys Val Leu Ser Thr
            100                 105                 110

Tyr Leu His Lys Arg Tyr Val Ile Ala Thr Ser Ser Gly Thr Asp Ala
        115                 120                 125

Ile Met Ile Gly Leu Leu Ala Leu Gly Leu Asn Pro Gly Asp Glu Val
130                 135                 140

Ile Met Pro Ala Asn Ser Phe Ser Ala Thr Glu Asn Ala Val Leu Ala
145                 150                 155                 160

Ser Gly Gly Val Pro Ile Tyr Val Asp Ile Asn Pro Gln Thr Phe Cys
                165                 170                 175

Ile Asp Pro Asp Lys Ile Glu Glu Ala Ile Thr Pro Tyr Thr Lys Phe
            180                 185                 190

Ile Leu Pro Val His Leu Tyr Gly Lys His Ser Asp Met Gln His Ile
        195                 200                 205

Arg Gln Ile Ala Asn Arg Tyr Lys Leu Lys Val Ile Glu Asp Ala Cys
210                 215                 220

Gln Gly Ile Gly Leu Thr Asp Leu Gly Lys Tyr Ala Asp Ile Thr Thr
225                 230                 235                 240

Leu Ser Phe Asn Pro Tyr Lys Asn Phe Gly Val Cys Gly Lys Ala Gly
                245                 250                 255

Ala Ile Ala Thr Asp Asn Glu Glu Leu Ala Lys Lys Cys Ile Gln Phe
            260                 265                 270

Ser Tyr His Gly Phe Glu Val Asn Val Lys Asn Lys Lys Val Ile Asn
        275                 280                 285

Phe Gly Phe Asn Ser Lys Met Asp Asn Leu Gln Ala Ala Ile Gly Leu
290                 295                 300

Glu Arg Met Lys Tyr Leu Ser Leu Asn Asn Phe Lys Arg Leu Phe Leu
305                 310                 315                 320

Ala Asp Arg Tyr Ile Thr Gln Leu Ala Glu Leu Gln Asn Lys Gly Tyr
                325                 330                 335

Ile Glu Leu Pro Glu Leu Ser Glu Asp His Val Trp His Leu Phe Pro
            340                 345                 350

Ile Lys Val Arg Thr Glu Asp Arg Ala Asp Ile Met Thr Lys Leu Asn
        355                 360                 365

Glu Asp Phe Gly Val Gln Thr Asp Val Tyr Tyr Pro Ile Leu Ser His
370                 375                 380
```

```
Met Gln Lys Thr Pro Leu Val Gln Asp Lys Tyr Ala Gly Leu Gln Leu
385                 390                 395                 400

Val His Thr Glu Lys Ala His Ser Gln Val Leu His Leu Pro Leu Tyr
                405                 410                 415

Pro Ser Phe Thr Leu Glu Glu Gln Asp Arg Val Met Glu Gly Leu Phe
                420                 425                 430

His Val Ile Lys Gln Glu Ile Gly Val
            435                 440

<210> SEQ ID NO 5
<211> LENGTH: 861
<212> TYPE: DNA
<213> ORGANISM: Bacillus subtilis
<220> FEATURE:
<221> NAME/KEY: misc_feature
<222> LOCATION: (1)..(861)
<223> OTHER INFORMATION: Coding sequence for kanosamine-6-phosphate
      (K6P) phosphatase (YhjK) from Genbank Accession No. Z99109

<400> SEQUENCE: 5
atgttattaa gcaagaaatc ggagtataaa acgttatcca cggttgaaca tcctcaatat      60
attgtttttt gtgattttga tgaaacgtat tttccgcata caatcgacga acaaaagcaa     120
caagacatct atgaactcga agactatcta gaacaaaaaa gtaaagatgg ggagctaata     180
atcggatggg ttactgggag cagtatagaa tctattctcg ataaaatggg acgaggaaaa     240
tttagatatt ttccgcattt tatagctagt gatcttggaa ctgaaattac gtacttttca     300
gagcataact tcggtcagca agataacaag tggaacagtc gcataaatga agggtttagt     360
aaagaaaagg ttgaaaaact tgtgaaacag ctgcatgaaa atcataacat tcttttgaat     420
cctcaaaccc aattaggaaa gtcacggtat aagcataact tctactatca ggaacaagat     480
gaaataaacg acaagaaaaa cctattagct attgaaaaaa tctgcgaaga atacggcgtt     540
tcagtaaata taaatcggtg taatcccttg gcaggcgatc cagaagacag ctatgatgta     600
gattttatcc ccataggggac aggaaagaat gaaattgtaa cgtttatgtt agagaaatac     660
aacctaaata ccgaaagagc tatcgcattt ggggatagtg aaatgatgt tcgtatgtta     720 cagacagtag ggaatggata tctgctaaaa aatgcaacac aggaagccaa aaacttgcac     780
aaccttataa ctgatagtga gtactcaaaa ggaattacta ataccttaaa aaaattaatt     840
ggattcatga ggaggaaata a                                               861

<210> SEQ ID NO 6
<211> LENGTH: 286
<212> TYPE: PRT
<213> ORGANISM: Bacillus subtilis
<220> FEATURE:
<221> NAME/KEY: MISC_FEATURE
<222> LOCATION: (1)..(286)
<223> OTHER INFORMATION: Kanosamine-6-phosphate (K6P) phosphatase (YhjK)
      from Genbank Accession No. CAB12894

<400> SEQUENCE: 6

Met Leu Leu Ser Lys Lys Ser Glu Tyr Lys Thr Leu Ser Thr Val Glu
1               5                   10                  15

His Pro Gln Tyr Ile Val Phe Cys Asp Phe Asp Glu Thr Tyr Phe Pro
                20                  25                  30

His Thr Ile Asp Glu Gln Lys Gln Gln Asp Ile Tyr Glu Leu Glu Asp
            35                  40                  45

Tyr Leu Glu Gln Lys Ser Lys Asp Gly Glu Leu Ile Ile Gly Trp Val
        50                  55                  60
```

```
Thr Gly Ser Ser Ile Glu Ser Ile Leu Asp Lys Met Gly Arg Gly Lys
 65                  70                  75                  80

Phe Arg Tyr Phe Pro His Phe Ile Ala Ser Asp Leu Gly Thr Glu Ile
             85                  90                  95

Thr Tyr Phe Ser Glu His Asn Phe Gly Gln Gln Asp Asn Lys Trp Asn
        100                 105                 110

Ser Arg Ile Asn Glu Gly Phe Ser Lys Glu Lys Val Glu Lys Leu Val
    115                 120                 125

Lys Gln Leu His Glu Asn His Asn Ile Leu Leu Asn Pro Gln Thr Gln
130                 135                 140

Leu Gly Lys Ser Arg Tyr Lys His Asn Phe Tyr Gln Glu Gln Asp
145                 150                 155                 160

Glu Ile Asn Asp Lys Lys Asn Leu Leu Ala Ile Glu Lys Ile Cys Glu
                165                 170                 175

Glu Tyr Gly Val Ser Val Asn Ile Asn Arg Cys Asn Pro Leu Ala Gly
            180                 185                 190

Asp Pro Glu Asp Ser Tyr Asp Val Asp Phe Ile Pro Ile Gly Thr Gly
        195                 200                 205

Lys Asn Glu Ile Val Thr Phe Met Leu Glu Lys Tyr Asn Leu Asn Thr
    210                 215                 220

Glu Arg Ala Ile Ala Phe Gly Asp Ser Gly Asn Asp Val Arg Met Leu
225                 230                 235                 240

Gln Thr Val Gly Asn Gly Tyr Leu Leu Lys Asn Ala Thr Gln Glu Ala
                245                 250                 255

Lys Asn Leu His Asn Leu Ile Thr Asp Ser Glu Tyr Ser Lys Gly Ile
            260                 265                 270

Thr Asn Thr Leu Lys Lys Leu Ile Gly Phe Met Arg Arg Lys
        275                 280                 285

<210> SEQ ID NO 7
<211> LENGTH: 1326
<212> TYPE: DNA
<213> ORGANISM: Amycolatopsis mediterranei
<220> FEATURE:
<221> NAME/KEY: misc_feature
<222> LOCATION: (1)..(1326)
<223> OTHER INFORMATION: Coding sequence for 4-amino-3,4-dideoxy-D-
      arabino-heptulosonic acid 7-phosphate (aminoDAHP) synthase (RifH)
      from Genbank Accession No. AF040570

<400> SEQUENCE: 7
gtgaagcggc agccggactt cgcggcccac ggccgggcgg tcgaccgggt gctggccggc    60
cggctgagcg cggcgctggc ccggccggcc gcgcagcagc cgggctggcc ggacgccgag   120
cgggcggccg aggtgatcga gctgctgcac gacgccgagc cgatcgtggc gccggaggag   180
accgcacggt tgcgcgcccg gctcgcgtcg gtcgcccgcg gcgaggcgtt cctgctgcag   240
ggcggggact gcgcggagac gttcgccggc aacaccgagc cgcacctgcg gccaacctc    300 ggggtgctgg cgcggatggg cgaagtgctg gccgaggcgg ccggcctgcc ggtggtcaag   360
atcgcccgga tggccgggca gttcgccaag ccgcggtccc ggaccgtcga cgcgctgggc   420
ctgccggtgt accggggcga catcgtgaac tccccggagt gcacggtcgc gcccggacc   480 cccgaccccg accggatgct gctggcatac gcccacgccg ccggcgcgat ggacctcgtc   540
cgcaagctct gcgccgaggg cctcgaagaa cccctggcgg cgcaggtggt gctcgcgggc   600
gcccgccgcg cgtcgtcgcc cggcgggcgg ccgttcccgg acttcggccg gccaccgcgc   660
ccggccgaga tctacgtcag ccacgaaatg ctcctgctcg actacgagcg ggccgtcctg   720
```

```
cggacggatt ccagcgggcc ggaaccgcgg ctgtccagcg ggctggcgca cttcctgtgg      780
atcggcgagc gccccgccag ctcgacggcg cccacatcga cgttcgcgga gctgctgtcc      840
aacccgatcg ggctgaagct ggggccgagc tgcaccccgg aggaggtcgt cgagtacgtg      900
cggcggctcg acccgcaccg cacgccgggc cggctgacgc tggtcagccg gatgggcac       960 gcccaggtcc gggagctcct cccgccgatc gtggagaagg tcgccgcctc cgggcacgag     1020
gtgatctggc agtgcgaccc gatgcacggc aacacccgga cctcgggcaa cggctacaag     1080
acccggcact cggccacgt cgtcgccgag ctggccggct tcttcgccgt gcaccggcag      1140
ctcggcaccc atcccggcgg catccacgtc gaggtgaccg cgacgacgt gacggaatgc      1200 ctcggcgggg ccgcgggcat cgcggaggcc gacctgcccg accgctacct gaccgcctgc     1260
gatccgcggc tcaacgccga ccagtcggtc gaactcgcgt cgcgatcgc gaagatgctg      1320 cgctag                                                                 1326
```

<210> SEQ ID NO 8
<211> LENGTH: 441
<212> TYPE: PRT
<213> ORGANISM: Amycolatopsis mediterranei
<220> FEATURE:
<221> NAME/KEY: MISC_FEATURE
<222> LOCATION: (1)..(441)
<223> OTHER INFORMATION: 4-amino-3,4-dideoxy-D-arabino-heptulosonic acid 7-phosphate (aminoDAHP) synthase (RifH) from Genbank Accession No. AAC01718

<400> SEQUENCE: 8

```
Met Lys Arg Gln Pro Asp Phe Ala Ala His Gly Arg Ala Val Asp Arg
1               5                   10                  15

Val Leu Ala Gly Arg Leu Ser Ala Leu Ala Arg Pro Ala Ala Gln
            20                  25                  30

Gln Pro Gly Trp Pro Asp Ala Glu Arg Ala Ala Glu Val Ile Glu Leu
        35                  40                  45

Leu His Asp Ala Glu Pro Ile Val Ala Pro Glu Glu Thr Ala Arg Leu
    50                  55                  60

Arg Ala Arg Leu Ala Ser Val Ala Arg Gly Glu Ala Phe Leu Leu Gln
65                  70                  75                  80

Gly Gly Asp Cys Ala Glu Thr Phe Ala Gly Asn Thr Glu Pro His Leu
                85                  90                  95

Arg Ala Asn Leu Gly Val Leu Ala Arg Met Gly Glu Val Leu Ala Glu
            100                 105                 110

Ala Ala Gly Leu Pro Val Val Lys Ile Ala Arg Met Ala Gly Gln Phe
        115                 120                 125

Ala Lys Pro Arg Ser Arg Thr Val Asp Ala Leu Gly Leu Pro Val Tyr
    130                 135                 140

Arg Gly Asp Ile Val Asn Ser Pro Glu Cys Thr Val Ala Ala Arg Thr
145                 150                 155                 160

Pro Asp Pro His Arg Met Leu Leu Ala Tyr Ala His Ala Ala Gly Ala
                165                 170                 175

Met Asp Leu Val Arg Lys Leu Cys Ala Glu Gly Leu Glu Glu Pro Leu
            180                 185                 190

Ala Ala Gln Val Val Leu Ala Gly Ala Arg Arg Ala Ser Ser Pro Gly
        195                 200                 205

Gly Arg Pro Phe Pro Asp Phe Gly Arg Pro Arg Pro Ala Glu Ile
    210                 215                 220

Tyr Val Ser His Glu Met Leu Leu Leu Asp Tyr Glu Arg Ala Val Leu
```

```
                    225                 230                 235                 240
Arg Thr Asp Ser Ser Gly Pro Glu Pro Arg Leu Ser Ser Gly Leu Ala
                245                 250                 255

His Phe Leu Trp Ile Gly Glu Arg Pro Ala Ser Ser Thr Ala Pro Thr
            260                 265                 270

Ser Thr Phe Ala Glu Leu Leu Ser Asn Pro Ile Gly Leu Lys Leu Gly
        275                 280                 285

Pro Ser Cys Thr Pro Glu Glu Val Val Glu Tyr Val Arg Arg Leu Asp
    290                 295                 300

Pro His Arg Thr Pro Gly Arg Leu Thr Leu Val Ser Arg Met Gly His
305                 310                 315                 320

Ala Gln Val Arg Glu Leu Leu Pro Pro Ile Val Glu Lys Val Ala Ala
                325                 330                 335

Ser Gly His Glu Val Ile Trp Gln Cys Asp Pro Met His Gly Asn Thr
            340                 345                 350

Arg Thr Ser Gly Asn Gly Tyr Lys Thr Arg His Phe Gly His Val Val
        355                 360                 365

Ala Glu Leu Ala Gly Phe Phe Ala Val His Arg Gln Leu Gly Thr His
    370                 375                 380

Pro Gly Gly Ile His Val Glu Val Thr Gly Asp Asp Val Thr Glu Cys
385                 390                 395                 400

Leu Gly Gly Ala Ala Gly Ile Ala Glu Ala Asp Leu Pro Asp Arg Tyr
                405                 410                 415

Leu Thr Ala Cys Asp Pro Arg Leu Asn Ala Asp Gln Ser Val Glu Leu
            420                 425                 430

Ala Phe Ala Ile Ala Lys Met Leu Arg
        435                 440

<210> SEQ ID NO 9
<211> LENGTH: 1650
<212> TYPE: DNA
<213> ORGANISM: Escherichia coli
<220> FEATURE:
<221> NAME/KEY: misc_feature
<222> LOCATION: (1)..(1650)
<223> OTHER INFORMATION: Coding sequence for phosphoglucose isomerase
      (Pgi) from Genbank Accession No. NC_000913

<400> SEQUENCE: 9
atgaaaaaca tcaatccaac gcagaccgct gcctggcagg cactacagaa acacttcgat      60
gaaatgaaag acgttacgat cgccgatctt tttgctaaag acggcgatcg tttttctaag     120
ttctccgcaa ccttcgacga tcagatgctg gtggattact ccaaaaaccg catcactgaa     180
gagacgctgg cgaaattaca ggatctggcg aaagagtgcg atctggcggg cgcgattaag     240
tcgatgttct ctggcgagaa gatcaaccgc actgaaaaacc gcgccgtgct gcacgtagcg     300
ctgcgtaacc gtagcaatac cccgattttg gttgatggca agacgtaat gccggaagtc     360 aacgcggtgc tggagaagat gaaaaccttc tcagaagcga ttatttccgg tgagtggaaa     420
ggttataccg gcaaagcaat cactgacgta gtgaacatcg gatcggcgg ttctgacctc     480 ggcccataca tggtgaccga agctctgcgt ccgtacaaaa accacctgaa catgcacttt     540
gtttctaacg tcgatgggac tcacatcgcg gaagtgctga aaaagtaaa cccggaaacc     600 acgctgttct tggtagcatc taaaaccttc accactcagg aaactatgac caacgcccat     660
agcgcgcgtg actggttcct gaaagcggca ggtgatgaaa acacgttgc aaaacacttt     720 gcggcgcttt ccaccaatgc caaagccgtt ggcgagtttg gtattgatac tgccaacatg     780
```

-continued

```
ttcgagttct gggactgggt tggcggccgt tactctttgt ggtcagcgat tggcctgtcg    840
attgttctct ccatcggctt tgataacttc gttgaactgc tttccggcgc acacgcgatg    900
gacaagcatt tctccaccac gcctgccgag aaaaacctgc ctgtactgct ggcgctgatt    960
ggcatctggt acaacaattt ctttggtgcg aaactgaag  cgattctgcc gtatgaccag   1020
tatatgcacc gtttcgcggc gtacttccag cagggcaata tggagtccaa cggtaagtat   1080
gttgaccgta acggtaacgt tgtggattac cagactggcc cgattatctg gggtgaacca   1140
ggcactaacg gtcagcacgc gttctaccag ctgatccacc agggaaccaa aatggtaccg   1200
tgcgatttca tcgctccggc tatcacccat aacccgctct ctgatcatca ccagaaactg   1260
ctgtctaact tcttcgccca gaccgaagcg ctggcgtttg gtaaatcccg cgaagtggtt   1320
gagcaggaat atcgtgatca gggtaaagat ccggcaacgc ttgactacgt ggtgccgttc   1380
aaagtattcg aaggtaaccg cccgaccaac tccatcctgc tgcgtgaaat cactccgttc   1440
agcctgggtg cgttgattgc gctgtatgag cacaaaatct ttactcaggg cgtgatcctg   1500
aacatcttca ccttcgacca gtggggcgtg gaactgggta acagctggc  gaaccgtatt   1560 ctgccagagc tgaaagatga taagaaatc agcagccacg atagctcgac caatggtctg   1620
attaaccgct ataaagcgtg gcgcggttaa                                   1650
```

<210> SEQ ID NO 10
<211> LENGTH: 549
<212> TYPE: PRT
<213> ORGANISM: Escherichia coli
<220> FEATURE:
<221> NAME/KEY: MISC_FEATURE
<222> LOCATION: (1)..(549)
<223> OTHER INFORMATION: Phosphoglucose isomerase (Pgi) from Genbank
      Accession No. NP_418449

<400> SEQUENCE: 10

```
Met Lys Asn Ile Asn Pro Thr Gln Thr Ala Ala Trp Gln Ala Leu Gln
1               5                   10                  15

Lys His Phe Asp Glu Met Lys Asp Val Thr Ile Ala Asp Leu Phe Ala
            20                  25                  30

Lys Asp Gly Asp Arg Phe Ser Lys Phe Ser Ala Thr Phe Asp Asp Gln
        35                  40                  45

Met Leu Val Asp Tyr Ser Lys Asn Arg Ile Thr Glu Glu Thr Leu Ala
    50                  55                  60

Lys Leu Gln Asp Leu Ala Lys Glu Cys Asp Leu Ala Gly Ala Ile Lys
65                  70                  75                  80

Ser Met Phe Ser Gly Glu Lys Ile Asn Arg Thr Glu Asn Arg Ala Val
                85                  90                  95

Leu His Val Ala Leu Arg Asn Arg Ser Asn Thr Pro Ile Leu Val Asp
            100                 105                 110

Gly Lys Asp Val Met Pro Glu Val Asn Ala Val Leu Glu Lys Met Lys
        115                 120                 125

Thr Phe Ser Glu Ala Ile Ile Ser Gly Glu Trp Lys Gly Tyr Thr Gly
    130                 135                 140

Lys Ala Ile Thr Asp Val Val Asn Ile Gly Ile Gly Gly Ser Asp Leu
145                 150                 155                 160

Gly Pro Tyr Met Val Thr Glu Ala Leu Arg Pro Tyr Lys Asn His Leu
                165                 170                 175

Asn Met His Phe Val Ser Asn Val Asp Gly Thr His Ile Ala Glu Val
            180                 185                 190

Leu Lys Lys Val Asn Pro Glu Thr Thr Leu Phe Leu Val Ala Ser Lys
```

```
                    195                 200                 205
Thr Phe Thr Thr Gln Glu Thr Met Thr Asn Ala His Ser Ala Arg Asp
210                 215                 220

Trp Phe Leu Lys Ala Ala Gly Asp Glu Lys His Val Ala Lys His Phe
225                 230                 235                 240

Ala Ala Leu Ser Thr Asn Ala Lys Ala Val Gly Glu Phe Gly Ile Asp
                245                 250                 255

Thr Ala Asn Met Phe Glu Phe Trp Asp Trp Val Gly Gly Arg Tyr Ser
                260                 265                 270

Leu Trp Ser Ala Ile Gly Leu Ser Ile Val Leu Ser Ile Gly Phe Asp
            275                 280                 285

Asn Phe Val Glu Leu Leu Ser Gly Ala His Ala Met Asp Lys His Phe
        290                 295                 300

Ser Thr Thr Pro Ala Glu Lys Asn Leu Pro Val Leu Leu Ala Leu Ile
305                 310                 315                 320

Gly Ile Trp Tyr Asn Asn Phe Phe Gly Ala Glu Thr Glu Ala Ile Leu
                325                 330                 335

Pro Tyr Asp Gln Tyr Met His Arg Phe Ala Ala Tyr Phe Gln Gln Gly
                340                 345                 350

Asn Met Glu Ser Asn Gly Lys Tyr Val Asp Arg Asn Gly Asn Val Val
            355                 360                 365

Asp Tyr Gln Thr Gly Pro Ile Ile Trp Gly Glu Pro Gly Thr Asn Gly
370                 375                 380

Gln His Ala Phe Tyr Gln Leu Ile His Gln Gly Thr Lys Met Val Pro
385                 390                 395                 400

Cys Asp Phe Ile Ala Pro Ala Ile Thr His Asn Pro Leu Ser Asp His
                405                 410                 415

His Gln Lys Leu Leu Ser Asn Phe Phe Ala Gln Thr Glu Ala Leu Ala
            420                 425                 430

Phe Gly Lys Ser Arg Glu Val Val Glu Gln Glu Tyr Arg Asp Gln Gly
        435                 440                 445

Lys Asp Pro Ala Thr Leu Asp Tyr Val Val Pro Phe Lys Val Phe Glu
450                 455                 460

Gly Asn Arg Pro Thr Asn Ser Ile Leu Leu Arg Glu Ile Thr Pro Phe
465                 470                 475                 480

Ser Leu Gly Ala Leu Ile Ala Leu Tyr Glu His Lys Ile Phe Thr Gln
                485                 490                 495

Gly Val Ile Leu Asn Ile Phe Thr Phe Asp Gln Trp Gly Val Glu Leu
            500                 505                 510

Gly Lys Gln Leu Ala Asn Arg Ile Leu Pro Glu Leu Lys Asp Asp Lys
        515                 520                 525

Glu Ile Ser Ser His Asp Ser Ser Thr Asn Gly Leu Ile Asn Arg Tyr
530                 535                 540

Lys Ala Trp Arg Gly
545

<210> SEQ ID NO 11
<211> LENGTH: 1992
<212> TYPE: DNA
<213> ORGANISM: Escherichia coli
<220> FEATURE:
<221> NAME/KEY: misc_feature
<222> LOCATION: (1)..(1992)
<223> OTHER INFORMATION: Coding sequence for transketolase (TktA) from
      Genbank Accession No. NC_000913

<400> SEQUENCE: 11
```

```
atgtcctcac gtaaagagct tgccaatgct attcgtgcgc tgagcatgga cgcagtacag      60
aaagccaaat ccggtcaccc gggtgcccct atgggtatgg ctgacattgc cgaagtcctg     120
tggcgtgatt tcctgaaaca caacccgcag aatccgtcct gggctgaccg tgaccgcttc     180
gtgctgtcca acggccacgg ctccatgctg atctacagcc tgctgcacct caccggttac     240
gatctgccga tggaagaact gaaaaacttc cgtcagctgc actctaaaac tccgggtcac     300
ccggaagtgg gttacaccgc tggtgtggaa accaccaccg tccgctgggt cagggtatt     360 gccaacgcag tcggtatggc gattgcagaa aaaacgctgg cggcgcagtt taaccgtccg     420
ggccacgaca ttgtcgacca ctacacctac gccttcatgg gcgacggctg catgatggaa     480
ggcatctccc acgaagtttg ctctctggcg gtacgctga agctgggtaa actgattgca     540
ttctacgatg acaacggtat ttctatcgat ggtcacgttg aaggctggtt caccgacgac     600
accgcaatgc gtttcgaagc ttacggctgg cacgttattc gcacatcga cggtcatgac     660 gcggcatcta tcaaacgcgc agtagaagaa gcgcgcgcag tgactgacaa accttccctg     720
ctgatgtgca aaaccatcat cggtttcggt tccccgaaca agccggtac ccacgactcc     780 cacggtgcgc cgctgggcga cgctgaaatt gccctgaccc gcaacaact gggctggaaa     840 tatgcgccgt cgaaatccc gtctgaaatc tatgctcagt gggatgcgaa agaagcaggc     900
caggcgaaag aatccgcatg gaacgagaaa ttcgctgctt acgcgaaagc ttatccgcag     960
gaagccgctg aatttacccg ccgtatgaaa ggcgaaatgc cgtctgactt cgacgctaaa    1020
gcgaaagagt tcatcgctaa actgcaggct aatccggcga aaatcgccag ccgtaaagcg    1080
tctcagaatg ctatcgaagc gttcggtccg ctgttgccgg aattcctcgg cggttctgct    1140
gacctggcgc cgtctaacct gacccctgtgg tctggttcta aagcaatcaa cgaagatgct    1200
gcgggtaact acatccacta cggtgttcgc gagttcggta tgaccgcgat tgctaacggt    1260
atctccctgc acggtggctt cctgccgtac acctccacct tcctgatgtt cgtggaatac    1320
gcacgtaacg ccgtacgtat ggctgcgctg atgaaacagc gtcaggtgat ggtttacacc    1380
cacgactcca tcggtctggg cgaagacggc ccgactcacc agccggttga gcaggtcgct    1440
tctctgcgcg taaccccgaa catgtctaca tggcgtccgt gtgaccaggt tgaatccgcg    1500
gtcgcgtgga aatacggtgt tgagcgtcag gacggcccga ccgcactgat cctctcccgt    1560
cagaacctgg cgcagcagga acgaactgaa gagcaactgg caaacatcgc gcgcggtggt    1620
tatgtgctga agactgcgc cggtcagccg gaactgattt tcatcgctac cggttcagaa    1680
gttgaactgg ctgttgctgc ctacgaaaaa ctgactgccg aaggcgtgaa agcgcgcgtg    1740
gtgtccatgc cgtctaccga cgcatttgac aagcaggatg ctgcttaccg tgaatccgta    1800
ctgccgaaag cggttactgc acgcgttgct gtagaagcgg gtattgctga ctactggtac    1860
aagtatgttg gcctgaacgg tgctatcgtc ggtatgacca ccttcggtga atctgctccg    1920
gcagagctgc tgtttgaaga gttcggcttc actgttgata cgttgttgc gaaagcaaaa    1980 gaactgctgt aa                                                         1992
```

<210> SEQ ID NO 12
<211> LENGTH: 663
<212> TYPE: PRT
<213> ORGANISM: Escherichia coli
<220> FEATURE:
<221> NAME/KEY: MISC_FEATURE
<222> LOCATION: (1)..(663)
<223> OTHER INFORMATION: Transketolase (TktA) from Genbank Accession No. YP_026188

<400> SEQUENCE: 12

```
Met Ser Ser Arg Lys Glu Leu Ala Asn Ala Ile Arg Ala Leu Ser Met
 1               5                  10                  15

Asp Ala Val Gln Lys Ala Lys Ser Gly His Pro Gly Ala Pro Met Gly
            20                  25                  30

Met Ala Asp Ile Ala Glu Val Leu Trp Arg Asp Phe Leu Lys His Asn
        35                  40                  45

Pro Gln Asn Pro Ser Trp Ala Asp Arg Asp Arg Phe Val Leu Ser Asn
    50                  55                  60

Gly His Gly Ser Met Leu Ile Tyr Ser Leu Leu His Leu Thr Gly Tyr
 65                  70                  75                  80

Asp Leu Pro Met Glu Glu Leu Lys Asn Phe Arg Gln Leu His Ser Lys
                85                  90                  95

Thr Pro Gly His Pro Glu Val Gly Tyr Thr Ala Gly Val Glu Thr Thr
            100                 105                 110

Thr Gly Pro Leu Gly Gln Gly Ile Ala Asn Ala Val Gly Met Ala Ile
            115                 120                 125

Ala Glu Lys Thr Leu Ala Ala Gln Phe Asn Arg Pro Gly His Asp Ile
    130                 135                 140

Val Asp His Tyr Thr Tyr Ala Phe Met Gly Asp Gly Cys Met Met Glu
145                 150                 155                 160

Gly Ile Ser His Glu Val Cys Ser Leu Ala Gly Thr Leu Lys Leu Gly
                165                 170                 175

Lys Leu Ile Ala Phe Tyr Asp Asp Asn Gly Ile Ser Ile Asp Gly His
            180                 185                 190

Val Glu Gly Trp Phe Thr Asp Asp Thr Ala Met Arg Phe Glu Ala Tyr
        195                 200                 205

Gly Trp His Val Ile Arg Asp Ile Asp Gly His Asp Ala Ala Ser Ile
    210                 215                 220

Lys Arg Ala Val Glu Glu Ala Arg Ala Val Thr Asp Lys Pro Ser Leu
225                 230                 235                 240

Leu Met Cys Lys Thr Ile Ile Gly Phe Gly Ser Pro Asn Lys Ala Gly
                245                 250                 255

Thr His Asp Ser His Gly Ala Pro Leu Gly Asp Ala Glu Ile Ala Leu
            260                 265                 270

Thr Arg Glu Gln Leu Gly Trp Lys Tyr Ala Pro Phe Glu Ile Pro Ser
        275                 280                 285

Glu Ile Tyr Ala Gln Trp Asp Ala Lys Glu Ala Gly Gln Ala Lys Glu
    290                 295                 300

Ser Ala Trp Asn Glu Lys Phe Ala Ala Tyr Lys Ala Tyr Pro Gln
305                 310                 315                 320

Glu Ala Ala Glu Phe Thr Arg Arg Met Lys Gly Glu Met Pro Ser Asp
                325                 330                 335

Phe Asp Ala Lys Ala Lys Glu Phe Ile Ala Lys Leu Gln Ala Asn Pro
            340                 345                 350

Ala Lys Ile Ala Ser Arg Lys Ala Ser Gln Asn Ala Ile Glu Ala Phe
        355                 360                 365

Gly Pro Leu Leu Pro Glu Phe Leu Gly Gly Ser Ala Asp Leu Ala Pro
    370                 375                 380

Ser Asn Leu Thr Leu Trp Ser Gly Ser Lys Ala Ile Asn Glu Asp Ala
385                 390                 395                 400

Ala Gly Asn Tyr Ile His Tyr Gly Val Arg Glu Phe Gly Met Thr Ala
                405                 410                 415
```

```
Ile Ala Asn Gly Ile Ser Leu His Gly Gly Phe Leu Pro Tyr Thr Ser
            420                 425                 430

Thr Phe Leu Met Phe Val Glu Tyr Ala Arg Asn Ala Val Arg Met Ala
        435                 440                 445

Ala Leu Met Lys Gln Arg Gln Val Met Val Tyr Thr His Asp Ser Ile
    450                 455                 460

Gly Leu Gly Glu Asp Gly Pro Thr His Gln Pro Val Glu Gln Val Ala
465                 470                 475                 480

Ser Leu Arg Val Thr Pro Asn Met Ser Thr Trp Arg Pro Cys Asp Gln
                485                 490                 495

Val Glu Ser Ala Val Ala Trp Lys Tyr Gly Val Glu Arg Gln Asp Gly
            500                 505                 510

Pro Thr Ala Leu Ile Leu Ser Arg Gln Asn Leu Ala Gln Gln Glu Arg
        515                 520                 525

Thr Glu Glu Gln Leu Ala Asn Ile Ala Arg Gly Gly Tyr Val Leu Lys
    530                 535                 540

Asp Cys Ala Gly Gln Pro Glu Leu Ile Phe Ile Ala Thr Gly Ser Glu
545                 550                 555                 560

Val Glu Leu Ala Val Ala Ala Tyr Glu Lys Leu Thr Ala Glu Gly Val
                565                 570                 575

Lys Ala Arg Val Val Ser Met Pro Ser Thr Asp Ala Phe Asp Lys Gln
            580                 585                 590

Asp Ala Ala Tyr Arg Glu Ser Val Leu Pro Lys Ala Val Thr Ala Arg
        595                 600                 605

Val Ala Val Glu Ala Gly Ile Ala Asp Tyr Trp Tyr Lys Tyr Val Gly
    610                 615                 620

Leu Asn Gly Ala Ile Val Gly Met Thr Thr Phe Gly Glu Ser Ala Pro
625                 630                 635                 640

Ala Glu Leu Leu Phe Glu Glu Phe Gly Phe Thr Val Asp Asn Val Val
                645                 650                 655

Ala Lys Ala Lys Glu Leu Leu
            660

<210> SEQ ID NO 13
<211> LENGTH: 1089
<212> TYPE: DNA
<213> ORGANISM: Escherichia coli
<220> FEATURE:
<221> NAME/KEY: misc_feature
<222> LOCATION: (1)..(1089)
<223> OTHER INFORMATION: Coding sequence for 3-dehydroquinate (DHQ)
      synthase (AroB) from Genbank Accession No. NC_000913

<400> SEQUENCE: 13
atggagagga ttgtcgttac tctcggggaa cgtagttacc caattaccat cgcatctggt      60
ttgtttaatg aaccagcttc attcttaccg ctgaaatcgg gcgagcaggt catgttggtc     120
accaacgaaa ccctggctcc tctgtatctc gataaggtcc gcggcgtact tgaacaggcg     180
ggtgttaacg tcgatagcgt tatcctccct gacggcgagc agtataaaag cctggctgta     240
ctcgataccg tctttacggc gttgttacaa aaaccgcatg gtcgcgatac tacgctggtg     300
gcgcttggcg gcggcgtagt gggcgatctg accggcttcg cggcggcgag ttatcagcgc     360
ggtgtccgtt tcattcaagt cccgacgacg ttactgtcgc aggtcgattc ctccgttggc     420
ggcaaaactg cggtcaacca tcccctcggt aaaaacatga ttggcgcgtt ctaccaacct     480
gcttcagtgg tggtggatct cgactgtctg aaaacgcttc cccgcgtga gttagcgtcg     540 gggctggcag aagtcatcaa atacggcatt attcttgacg gtgcgttttt taactggctg     600
```

```
gaagagaatc tggatgcgtt gttgcgtctg gacggtccgg caatggcgta ctgtattcgc    660
cgttgttgtg aactgaaggc agaagttgtc gccgccgacg agcgcgaaac cgggttacgt    720
gctttactga atctgggaca caccttggt catgccattg aagctgaaat ggggtatggc     780
aattggttac atggtgaagc ggtcgctgcg ggtatggtga tggcggcgcg acgtcggaa     840 cgtctcgggc agtttagttc tgccgaaacg cagcgtatta taaccctgct caagcgggct    900
gggttaccgg tcaatgggcc gcgcgaaatg tccgcgcagg cgtatttacc gcatatgctg    960
cgtgacaaga aagtccttgc gggagagatg cgcttaattc ttccgttggc aattggtaag    1020
agtgaagttc gcagcggcgt ttcgcacgag cttgttctta cgccattgc cgattgtcaa     1080 tcagcgtaa                                                             1089
```

<210> SEQ ID NO 14
<211> LENGTH: 362
<212> TYPE: PRT
<213> ORGANISM: Escherichia coli
<220> FEATURE:
<221> NAME/KEY: MISC_FEATURE
<222> LOCATION: (1)..(362)
<223> OTHER INFORMATION: 3-dehydroquinate (DHQ) synthase (AroB) from
      Genbank Accession No. NP_417848

<400> SEQUENCE: 14

```
Met Glu Arg Ile Val Val Thr Leu Gly Glu Arg Ser Tyr Pro Ile Thr
1               5                   10                  15

Ile Ala Ser Gly Leu Phe Asn Glu Pro Ala Ser Phe Leu Pro Leu Lys
            20                  25                  30

Ser Gly Glu Gln Val Met Leu Val Thr Asn Glu Thr Leu Ala Pro Leu
        35                  40                  45

Tyr Leu Asp Lys Val Arg Gly Val Leu Glu Gln Ala Gly Val Asn Val
    50                  55                  60

Asp Ser Val Ile Leu Pro Asp Gly Glu Gln Tyr Lys Ser Leu Ala Val
65                  70                  75                  80

Leu Asp Thr Val Phe Thr Ala Leu Leu Gln Lys Pro His Gly Arg Asp
                85                  90                  95

Thr Thr Leu Val Ala Leu Gly Gly Gly Val Val Gly Asp Leu Thr Gly
            100                 105                 110

Phe Ala Ala Ala Ser Tyr Gln Arg Gly Val Arg Phe Ile Gln Val Pro
        115                 120                 125

Thr Thr Leu Leu Ser Gln Val Asp Ser Ser Val Gly Gly Lys Thr Ala
    130                 135                 140

Val Asn His Pro Leu Gly Lys Asn Met Ile Gly Ala Phe Tyr Gln Pro
145                 150                 155                 160

Ala Ser Val Val Val Asp Leu Asp Cys Leu Lys Thr Leu Pro Pro Arg
                165                 170                 175

Glu Leu Ala Ser Gly Leu Ala Glu Val Ile Lys Tyr Gly Ile Ile Leu
            180                 185                 190

Asp Gly Ala Phe Phe Asn Trp Leu Glu Glu Asn Leu Asp Ala Leu Leu
        195                 200                 205

Arg Leu Asp Gly Pro Ala Met Ala Tyr Cys Ile Arg Arg Cys Cys Glu
    210                 215                 220

Leu Lys Ala Glu Val Val Ala Ala Asp Glu Arg Glu Thr Gly Leu Arg
225                 230                 235                 240

Ala Leu Leu Asn Leu Gly His Thr Phe Gly His Ala Ile Glu Ala Glu
                245                 250                 255
```

-continued

```
Met Gly Tyr Gly Asn Trp Leu His Gly Glu Ala Val Ala Ala Gly Met
            260                 265                 270

Val Met Ala Ala Arg Thr Ser Glu Arg Leu Gly Gln Phe Ser Ser Ala
        275                 280                 285

Glu Thr Gln Arg Ile Ile Thr Leu Leu Lys Arg Ala Gly Leu Pro Val
    290                 295                 300

Asn Gly Pro Arg Glu Met Ser Ala Gln Ala Tyr Leu Pro His Met Leu
305                 310                 315                 320

Arg Asp Lys Lys Val Leu Ala Gly Glu Met Arg Leu Ile Leu Pro Leu
                325                 330                 335

Ala Ile Gly Lys Ser Glu Val Arg Ser Gly Val Ser His Glu Leu Val
            340                 345                 350

Leu Asn Ala Ile Ala Asp Cys Gln Ser Ala
        355                 360

<210> SEQ ID NO 15
<211> LENGTH: 759
<212> TYPE: DNA
<213> ORGANISM: Escherichia coli
<220> FEATURE:
<221> NAME/KEY: misc_feature
<222> LOCATION: (1)..(759)
<223> OTHER INFORMATION: Coding sequence for 3-dehydroquinate (DHQ)
      dehydratase (AroD) from Genbank Accession No. NC_000913

<400> SEQUENCE: 15
atgaaaaccg taactgtaaa agatctcgtc attggtacgg gcgcacctaa aatcatcgtc      60
tcgctgatgg cgaaagatat cgccagcgtg aaatccgaag ctctcgccta tcgtgaagcg     120
gactttgata ttctggaatg gcgtgtggac cactatgccg acctctccaa tgtggagtct     180
gtcatggcgg cagcaaaaat tctccgtgag accatgccag aaaaaccgct gctgtttacc     240
ttccgcagtg ccaaagaagg cggcgagcag gcgatttcca ccgaggctta tattgcactc     300
aatcgtgcag ccatcgacag cggcctggtt gatatgatcg atctggagtt atttaccggt     360
gatgatcagg ttaaagaaac cgtcgcctac gcccacgcgc atgatgtgaa agtagtcatg     420
tccaaccatg acttccataa aacgccggaa gccgaagaaa tcattgcccg tctgcgcaaa     480
atgcaatcct tcgacgccga tattcctaag attgcgctga tgccgcaaag taccagcgat     540
gtgctgacgt tgcttgccgc gaccctggag atgcaggagc agtatgccga tgtccaattt     600
atcacgatgt cgatggcaaa aactggcgta atttctcgtc tggctggtga agtatttggc     660
tcggcggcaa cttttggtgc ggtaaaaaaa gcgtctgcgc agggcaaat ctcggtaaat     720 gatttgcgca cggtattaac tattttacac caggcataa                             759

<210> SEQ ID NO 16
<211> LENGTH: 252
<212> TYPE: PRT
<213> ORGANISM: Escherichia coli
<220> FEATURE:
<221> NAME/KEY: MISC_FEATURE
<222> LOCATION: (1)..(252)
<223> OTHER INFORMATION: 3-dehydroquinate (DHQ) dehydratase (AroD) from
      Genbank Accession No. NP_416208

<400> SEQUENCE: 16

Met Lys Thr Val Thr Val Lys Asp Leu Val Ile Gly Thr Gly Ala Pro
1               5                   10                  15

Lys Ile Ile Val Ser Leu Met Ala Lys Asp Ile Ala Ser Val Lys Ser
            20                  25                  30

Glu Ala Leu Ala Tyr Arg Glu Ala Asp Phe Asp Ile Leu Glu Trp Arg
```

```
                35                  40                  45
Val Asp His Tyr Ala Asp Leu Ser Asn Val Glu Ser Val Met Ala Ala
 50                  55                  60

Ala Lys Ile Leu Arg Glu Thr Met Pro Glu Lys Pro Leu Leu Phe Thr
 65                  70                  75                  80

Phe Arg Ser Ala Lys Glu Gly Gly Glu Gln Ala Ile Ser Thr Glu Ala
                 85                  90                  95

Tyr Ile Ala Leu Asn Arg Ala Ala Ile Asp Ser Gly Leu Val Asp Met
                100                 105                 110

Ile Asp Leu Glu Leu Phe Thr Gly Asp Asp Gln Val Lys Glu Thr Val
                115                 120                 125

Ala Tyr Ala His Ala His Asp Val Lys Val Val Met Ser Asn His Asp
130                 135                 140

Phe His Lys Thr Pro Glu Ala Glu Glu Ile Ile Ala Arg Leu Arg Lys
145                 150                 155                 160

Met Gln Ser Phe Asp Ala Asp Ile Pro Lys Ile Ala Leu Met Pro Gln
                165                 170                 175

Ser Thr Ser Asp Val Leu Thr Leu Leu Ala Ala Thr Leu Glu Met Gln
                180                 185                 190

Glu Gln Tyr Ala Asp Arg Pro Ile Ile Thr Met Ser Met Ala Lys Thr
                195                 200                 205

Gly Val Ile Ser Arg Leu Ala Gly Glu Val Phe Gly Ser Ala Ala Thr
            210                 215                 220

Phe Gly Ala Val Lys Lys Ala Ser Ala Pro Gly Gln Ile Ser Val Asn
225                 230                 235                 240

Asp Leu Arg Thr Val Leu Thr Ile Leu His Gln Ala
                245                 250

<210> SEQ ID NO 17
<211> LENGTH: 819
<212> TYPE: DNA
<213> ORGANISM: Escherichia coli
<220> FEATURE:
<221> NAME/KEY: misc_feature
<222> LOCATION: (1)..(819)
<223> OTHER INFORMATION: Coding sequence for shikimate dehydrogenase
      (AroE) from Genbank Accession No. NC_000913

<400> SEQUENCE: 17
atggaaacct atgctgtttt tggtaatccg atagcccaca gcaaatcgcc attcattcat     60
cagcaatttg ctcagcaact gaatattgaa catccctatg gcgcgtgtt ggcacccatc    120 aatgatttca tcaacacact gaacgctttc tttagtgctg gtggtaaagg tgcgaatgtg    180
acggtgcctt ttaagaaga ggcttttgcc agagcggatg agcttactga acgggcagcg    240
ttggctggtg ctgttaatac cctcatgcgg ttagaagatg acgcctgct gggtgacaat    300 accgatggtg taggcttgtt aagcgatctg aacgtctgt cttttatccg ccctggttta    360
cgtattctgc ttatcggcgc tggtggagca tctcgcggcg tactactgcc actcctttcc    420
ctggactgtg cggtgacaat aactaatcgg acggtatccc gcgcggaaga gttggctaaa    480
ttgtttgcgc acactggcag tattcaggcg ttgagtatgg acgaactgga aggtcatgag    540
tttgatctca ttattaatgc aacatccagt ggcatcagtg gtgatattcc ggcgatcccg    600
tcatcgctca ttcatccagg catttattgc tatgacatgt tctatcagaa aggaaaaact    660 cctttttctgg catggtgtga gcagcgagc tcaaagcgta atgctgatgg tttaggaatg    720
ctggtggcac aggcggctca tgcctttctt ctctggcacg tgttctgcc tgacgtagaa    780
```

<210> SEQ ID NO 18
<211> LENGTH: 272
<212> TYPE: PRT
<213> ORGANISM: Escherichia coli
<220> FEATURE:
<221> NAME/KEY: MISC_FEATURE
<222> LOCATION: (1)..(272)
<223> OTHER INFORMATION: Shikimate dehydrogenase (AroE) from Genbank Accession No. NP_417740

<400> SEQUENCE: 18

```
Met Glu Thr Tyr Ala Val Phe Gly Asn Pro Ile Ala His Ser Lys Ser
1               5                   10                  15

Pro Phe Ile His Gln Gln Phe Ala Gln Gln Leu Asn Ile Glu His Pro
            20                  25                  30

Tyr Gly Arg Val Leu Ala Pro Ile Asn Asp Phe Ile Asn Thr Leu Asn
        35                  40                  45

Ala Phe Phe Ser Ala Gly Gly Lys Gly Ala Asn Val Thr Val Pro Phe
    50                  55                  60

Lys Glu Glu Ala Phe Ala Arg Ala Asp Glu Leu Thr Glu Arg Ala Ala
65                  70                  75                  80

Leu Ala Gly Ala Val Asn Thr Leu Met Arg Leu Glu Asp Gly Arg Leu
                85                  90                  95

Leu Gly Asp Asn Thr Asp Gly Val Gly Leu Leu Ser Asp Leu Glu Arg
            100                 105                 110

Leu Ser Phe Ile Arg Pro Gly Leu Arg Ile Leu Leu Ile Gly Ala Gly
        115                 120                 125

Gly Ala Ser Arg Gly Val Leu Leu Pro Leu Leu Ser Leu Asp Cys Ala
    130                 135                 140

Val Thr Ile Thr Asn Arg Thr Val Ser Arg Ala Glu Glu Leu Ala Lys
145                 150                 155                 160

Leu Phe Ala His Thr Gly Ser Ile Gln Ala Leu Ser Met Asp Glu Leu
                165                 170                 175

Glu Gly His Glu Phe Asp Leu Ile Ile Asn Ala Thr Ser Ser Gly Ile
            180                 185                 190

Ser Gly Asp Ile Pro Ala Ile Pro Ser Ser Leu Ile His Pro Gly Ile
        195                 200                 205

Tyr Cys Tyr Asp Met Phe Tyr Gln Lys Gly Lys Thr Pro Phe Leu Ala
    210                 215                 220

Trp Cys Glu Gln Arg Gly Ser Lys Arg Asn Ala Asp Gly Leu Gly Met
225                 230                 235                 240

Leu Val Ala Gln Ala Ala His Ala Phe Leu Leu Trp His Gly Val Leu
                245                 250                 255

Pro Asp Val Glu Pro Val Ile Lys Gln Leu Gln Glu Glu Leu Ser Ala
            260                 265                 270
```

<210> SEQ ID NO 19
<211> LENGTH: 966
<212> TYPE: DNA
<213> ORGANISM: Escherichia coli
<220> FEATURE:
<221> NAME/KEY: misc_feature
<222> LOCATION: (1)..(966)
<223> OTHER INFORMATION: Coding sequence for glucose kinase (Glk) from Genbank Accession No. NC_000913

<400> SEQUENCE: 19
atgacaaagt atgcattagt cggtgatgtg ggcggcacca acgcacgtct tgctctgtgt        60

```
gatattgcca gtggtgaaat ctcgcaggct aagacctatt cagggcttga ttaccccagc    120
ctcgaagcgg tcattcgcgt ttatcttgaa gaacataagg tcgaggtgaa agacggctgt    180
attgccatcg cttgcccaat taccggtgac tgggtggcga tgaccaacca tacctgggcg    240
ttctcaattg ccgaaatgaa aaagaatctc ggttttagcc atctggaaat tattaacgat    300
tttaccgctg tatcgatggc gatcccgatg ctgaaaaaag agcatctgat tcagtttggt    360
ggcgcagaac cggtcgaagg taagcctatt gcggtttacg gtgccggaac ggggcttggg    420
gttgcgcatc tggtccatgt cgataagcgt tgggtaagct tgccaggcga aggcggtcac    480
gttgattttg cgccgaatag tgaagaagag gccattatcc tcgaaatatt gcgtgcggaa    540
attggtcatg tttcggcgga gcgcgtgctt tctggccctg gctggtgaa  tttgtatcgc    600 gcaattgtga agctgacaa  ccgcctgcca gaaaatctca gccaaaaga  tattaccgaa    660 cgcgcgctgg ctgacagctg caccgattgc cgccgcgcat tgtcgctgtt ttgcgtcatt    720
atgggccgtt tggcggcaa  tctggcgctc aatctcggga catttggcgg cgtgtttatt    780
gcgggcggta tcgtgccgcg cttccttgag ttcttcaaag cctccggttt ccgtgccgca    840
tttgaagata aagggcgctt taagaatat  gtccatgata ttccggtgta tctcatcgtc    900
catgacaatc cgggccttct cggttccggt gcacatttac gccagacctt aggtcacatt    960
ctgtaa                                                                966
```

<210> SEQ ID NO 20  
<211> LENGTH: 321  
<212> TYPE: PRT  
<213> ORGANISM: Escherichia coli  
<220> FEATURE:  
<221> NAME/KEY: MISC_FEATURE  
<222> LOCATION: (1)..(321)  
<223> OTHER INFORMATION: Glucose kinase (Glk) from Genbank Accession No. NP_416889

<400> SEQUENCE: 20

```
Met Thr Lys Tyr Ala Leu Val Gly Asp Val Gly Gly Thr Asn Ala Arg
1               5                   10                  15

Leu Ala Leu Cys Asp Ile Ala Ser Gly Glu Ile Ser Gln Ala Lys Thr
            20                  25                  30

Tyr Ser Gly Leu Asp Tyr Pro Ser Leu Glu Ala Val Ile Arg Val Tyr
        35                  40                  45

Leu Glu Glu His Lys Val Glu Val Lys Asp Gly Cys Ile Ala Ile Ala
    50                  55                  60

Cys Pro Ile Thr Gly Asp Trp Val Ala Met Thr Asn His Thr Trp Ala
65                  70                  75                  80

Phe Ser Ile Ala Glu Met Lys Lys Asn Leu Gly Phe Ser His Leu Glu
                85                  90                  95

Ile Ile Asn Asp Phe Thr Ala Val Ser Met Ala Ile Pro Met Leu Lys
            100                 105                 110

Lys Glu His Leu Ile Gln Phe Gly Gly Ala Glu Pro Val Glu Gly Lys
        115                 120                 125

Pro Ile Ala Val Tyr Gly Ala Gly Thr Gly Leu Gly Val Ala His Leu
    130                 135                 140

Val His Val Asp Lys Arg Trp Val Ser Leu Pro Gly Glu Gly Gly His
145                 150                 155                 160

Val Asp Phe Ala Pro Asn Ser Glu Glu Glu Ala Ile Ile Leu Glu Ile
                165                 170                 175

Leu Arg Ala Glu Ile Gly His Val Ser Ala Glu Arg Val Leu Ser Gly
```

-continued

```
                   180                 185                 190
Pro Gly Leu Val Asn Leu Tyr Arg Ala Ile Val Lys Ala Asp Asn Arg
        195                 200                 205

Leu Pro Glu Asn Leu Lys Pro Lys Asp Ile Thr Glu Arg Ala Leu Ala
        210                 215                 220

Asp Ser Cys Thr Asp Cys Arg Arg Ala Leu Ser Leu Phe Cys Val Ile
225                 230                 235                 240

Met Gly Arg Phe Gly Gly Asn Leu Ala Leu Asn Leu Gly Thr Phe Gly
                245                 250                 255

Gly Val Phe Ile Ala Gly Gly Ile Val Pro Arg Phe Leu Glu Phe Phe
                260                 265                 270

Lys Ala Ser Gly Phe Arg Ala Ala Phe Glu Asp Lys Gly Arg Phe Lys
        275                 280                 285

Glu Tyr Val His Asp Ile Pro Val Tyr Leu Ile Val His Asp Asn Pro
        290                 295                 300

Gly Leu Leu Gly Ser Gly Ala His Leu Arg Gln Thr Leu Gly His Ile
305                 310                 315                 320

Leu
```

US 7,977,077 B2

SYNTHESIS OF INTERMEDIATES OF OSELTAMIVIR CARBOXYLATES

CROSS-REFERENCE TO RELATED APPLICATIONS

The present application claims the benefit under 35 U.S.C. §119(e) of U.S. Provisional Application Ser. Nos. 60/763,485 and 60/763,484, both filed Jan. 30, 2006.

STATEMENT REGARDING FEDERALLY SPONSORED RESEARCH

Certain aspects, of the present inventions were developed with support under grant 5R01GM065541-04 from the National Institutes of Health. The U.S. Government may have rights in certain of these inventions.

BACKGROUND

The present disclosure relates to the biosynthetic production of 5-amino-5-deoxyshikimic acid or kanosamine and their conversion to oseltamivir carboxylates and other derivatives.

Aminoshikimate is an industrially important compound that can be used as a starting material in the formation of oseltamivir carboxylates for use in producing the antiviral drug formulation, TAMIFLU (Hoffmann-La Roche). Oseltamivir carboxylates are commercially produced using shikimic acid as a starting material. Traditionally, the shikimic acid has been isolated from plants, especially *Illicium* species, which include Chinese star anise (*I. verum*) and Japanese star anise (*I. anisatum*). Star anise seeds are industrially processed in a ten-stage procedure, which takes about a year, in order to obtain shikimic acid. A shortage of shikimic acid, sometimes attributed to insufficient quantities of star anise, has been cited as a potential impediment to the production of oseltamivir carboxylates. As a result, recombinant microbes, engineered to exhibit increased shikimic acid production, have been used to produce shikimic acid to help meet this need.

However, even with microbial synthesis of shikimic acid, the cost of converting shikimic acid to oseltamivir carboxylates has remained relatively constant. Two different major chemosynthetic routes have been reported for the conversion to oseltamivir phosphate, which is the active ingredient present in TAMIFLU, each of which utilizes many steps, e.g.: 10 steps, including three explosive and/or toxic azide derivatives; or 17 steps in an azide-free process. In both of these routes, about 4 of the steps are performed in order to add an amino group substituent at the 5-position of the shikimate ring. See, e.g., C. U. Kim et al., *J. Am. Chem. Soc.* 119(4): 681-90 (Jan. 29, 1997); J. C. Rohloff et al., *J. Org. Chem.* 63(13):4545-50 (Jun. 26, 1998); M. Karpf & R. Trussardi, *J. Org. Chem.* 66(6):2044-51 (Mar. 23, 2001); S. Abrecht et al., *Chimia* 58(9):621-29 (2004); Y.-Y. Yeung et al., *J. Am. Chem. Soc.* 128(19):6310-311 (May 17, 2006); Y. Fukuta et al., *J. Am. Chem. Soc.* 128(19):6312-13 (May 17, 2006); and T. Mita et al., *Org. Lett.* 9(2):259-62 (Jan. 18, 2007).

As a result, providing a process that does not require those steps can significantly improve both the speed and economics of the production of oseltamivir phosphate or other oseltamivir carboxylates. One way to help achieve this goal could be to provide biosynthetic 5-aminoshikimic acid, i.e. 5-amino-5-deoxyshikimic acid, as a starting material for the chemosynthetic oseltamivir phosphate production process.

Two biosynthetic routes for production of aminoshikimic acid have been reported. In the first, the wild-type bacterium, *Amycolatopsis mediterranei* (ATCC 21789), has been found capable of anabolic synthesis of aminoshikimate from glucose, using a biosynthetic route that involves formation of the high energy intermediate, UDP-glucose, transformation to UDP-kanosamine and then to kanosamine, followed by conversion of the kanosamine, in multiple steps, to aminoshikimate.

In the second route, two different organisms are used: 1) *Bacillus pumilus* (ATCC 21143), used for anabolic synthesis of kanosamine, also via the high energy UDP-glucose pathway; and 2) a recombinant *E. coli*, used to convert the resulting kanosamine to aminoshikimate. J. Guo & J. Frost, *Org. Lett.* 6(10):1585-88 (May 13, 2004) (published online Apr. 14, 2004 as DOI 10.1021/ol049666e); J. Guo & J. Frost, *J. Am. Chem. Soc.* 124(36):10642-43 (Sep. 11, 2002); also J. Guo & J. Frost, *J. Am. Chem. Soc.* 124(4):528-29 (Jan. 30, 2002). Yet, for commercial applications, this process would require two separate fermentations, with an intervening recovery of the kanosamine intermediate so as to at least partially remove *Bacillus*-expressed toxins and antimicrobial peptides therefrom. These multiple steps would introduce significant expense and decreased yields of aminoshikimate by loss of kanosamine.

Moreover, because both of these are high energy processes, they are metabolically expensive, and use of these processes would present commercially expensive routes to obtain an aminoshikimate starting material for oseltamivir phosphate production. A less energy-intensive process would be important in order to obtain an economically advantageous route.

As a result, it would be beneficial to provide a more efficient, less expensive route for biosynthesis of aminoshikimate. It would likewise be beneficial to provide an overall process for production of oseltamivir carboxylates that is similarly more efficient and less expensive than the current process. It would also be desirable to provide a process that can be used to produce other useful intermediates, as well.

SUMMARY

Some embodiments of the present invention provide improved processes for biosynthesis of aminoshikimate, and improved processes for oseltamivir production, which involve anabolic biosynthesis of aminoshikimate via a glucose-6-phosphate intermediate. Some embodiments of the present invention provide an improved biosynthetic route for production of kanosamine, which can be used for aminoshikimate biosynthesis or for other purposes. The biosyntheses of aminoshikimate or kanosamine are anabolic, using simple carbon sources, such as glucose, and do not require formation of high energy intermediates, such as UDP-glucose. These are also capable of operation in single cells of a variety of commonly used microbes that are amenable to very large scale cultures for commercial production of aminoshikimate or kanosamine; thus, the processes can, in some embodiments, be performed in a single fermentation.

Some embodiments of the present invention further provide:

Isolated or recombinant aminoshikimate biosynthesis enzyme systems that include (1) at least one 3-keto-D-glucose-6-phosphate (3KG6P) dehydrogenase, (2) at least one 3-keto-D-glucose-6-phosphate (3KG6P) transaminase, and (3) at least one 4-amino-3,4-dideoxy-D-arabino-heptulosonic acid 7-phosphate (aminoDAHP) synthase, the enzyme systems being capable of catalyzing conversion of glucose-6-phosphate (G6P) to 3-keto-D-glucose-6-phosphate (3KG6P), 3KG6P to kanosamine-6-phosphate (K6P), K6P to 1-imino-1-deoxy-D-erythrose-4-phosphate (iminoE4P), iminoE4P to 4-amino-3,4-dideoxy-D-arabino-heptulosonic acid 7-phosphate (aminoDAHP), and aminoDAHP to aminoshikimate;

Such enzyme systems further including (4) at least one phosphoglucose isomerase (Pgi); (5) at least one transketolase (TktA); (6) at least one 3-dehydroquinate (DHQ) synthase, 5-amino-3-dehydroquinate (aminoDHQ) synthase, or combination thereof; (7) at least one 3-dehydroquinate (DHQ) dehydratase, 5-amino-3-dehydroquinate (aminoDHQ) dehydratase, or combination thereof; and (8) at least one shikimate dehydrogenase, quinate/shikimate dehydrogenase, or aminoquinate/aminoshikimate dehydrogenase, or combination thereof; and optionally (9) at least one kanosamine-6-phosphate (K6P) phosphatase; and (10) at least one phosphoenolpyruvate:carbohydrate phosphotransferase system, a glucose kinase (Glk), or a kanosamine kinase.

Processes for producing 5-amino-5-deoxyshikimic acid (aminoshikimate) anabolically from a carbon source by use of such enzyme systems; nucleic acid encoding such enzyme systems; isolated or recombinant cells comprising such aminoshikimate biosynthesis enzyme systems or such nucleic acid;

Processes for preparing derivatives of aminoshikimate prepared by such anabolic processes by biosynthetically or chemosynthetically modifying the aminoshikimate; such processes that convert the aminoshikimate to an oseltamivir carboxylate, such as oseltamivir phosphate;

Aminoshikimic acid, aminoshikimic acid derivatives, oseltamivir carboxylates, and oseltamivir phosphate prepared by such processes; compositions comprising such aminoshikimic acid, aminoshikimic acid derivatives, oseltamivir carboxylates, and oseltamivir phosphate;

Isolated or recombinant kanosamine biosynthesis enzyme systems that include (1) at least one 3-keto-D-glucose-6-phosphate (3KG6P) dehydrogenase, (2) at least one 3-keto-D-glucose-6-phosphate (3KG6P) transaminase, and (3) at least one K6P phosphatase, the enzyme systems being capable of catalyzing the conversion of glucose-6-phosphate (G6P) to 3-keto-D-glucose-6-phosphate (3KG6P), 3KG6P to kanosamine-6-phosphate (K6P), and K6P to kanosamine;

Processes for producing kanosamine anabolically from a carbon source by use of such enzyme systems; nucleic acid encoding such enzyme systems; isolated or recombinant cells comprising such kanosamine biosynthesis enzyme systems or such nucleic acid;

Processes for preparing derivatives of kanosamine prepared by such anabolic processes by biosynthetically or chemosynthetically modifying the kanosamine;

Kanosamine and kanosamine derivatives prepared by such processes; compositions comprising such kanosamine and kanosamine derivatives;

Kits comprising nucleic acid encoding at least one enzyme of such an anabolic aminoshikimate or kanosamine enzyme system, with instructions for use thereof to produce an anabolic kanosamine or aminoshikimate biosynthesis enzyme system or to produce kanosamine, aminoshikimate, or a derivative thereof; and Kits comprising at least one enzyme of such an anabolic aminoshikimate or kanosamine enzyme system, with instructions for use thereof to produce an anabolic kanosamine or aminoshikimate biosynthesis enzyme system or to produce kanosamine, aminoshikimate, or a derivative thereof.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

Figure 3:
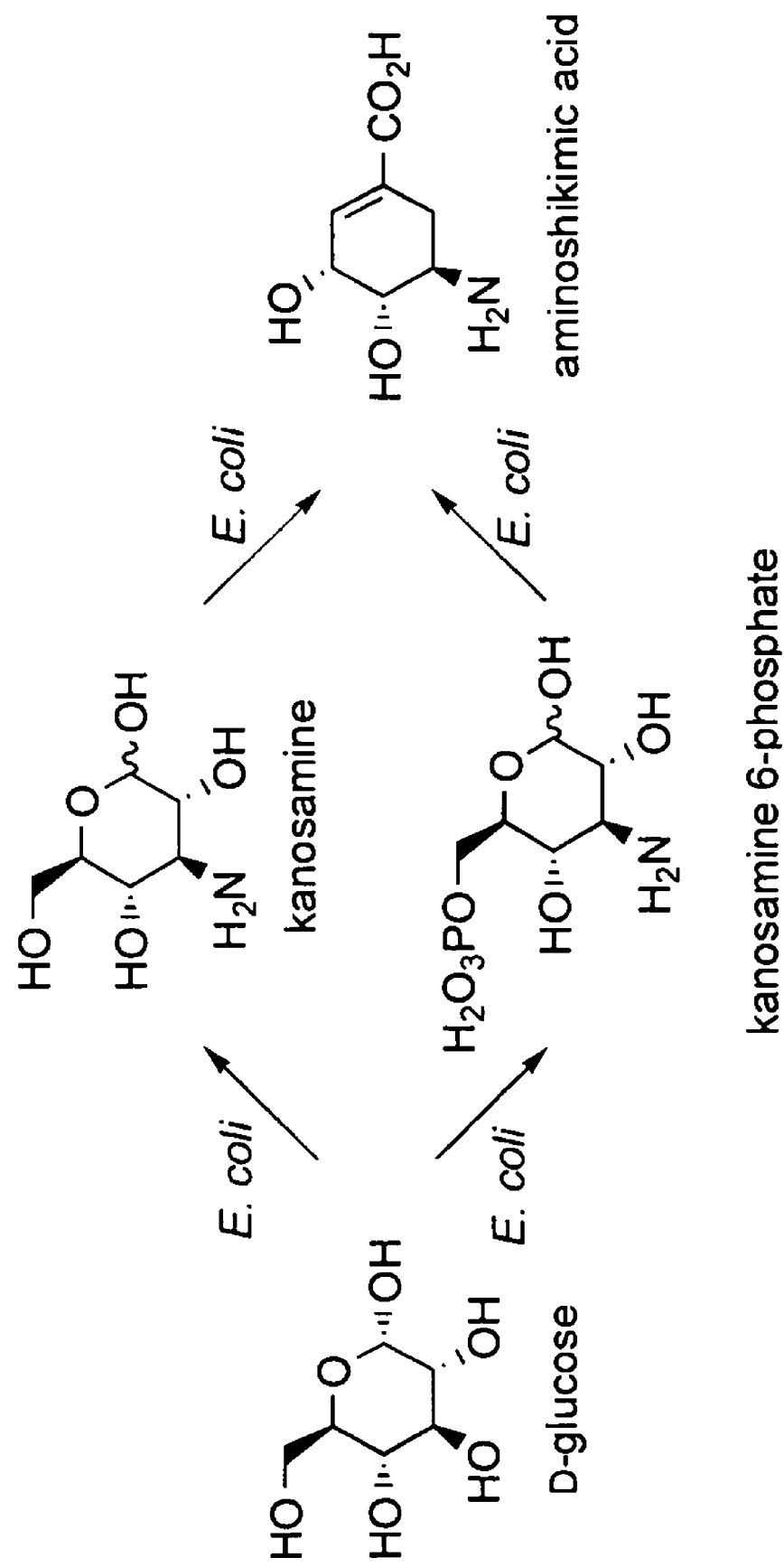

FIG. 3 schematically illustrates two different pathways hereof for aminoshikimate biosynthesis, one proceeding via a kanosamine intermediate and the other proceeding by a kanosamine-6-phosphate (K6P) intermediate without requiring formation of kanosamine itself; it also illustrates that either kanosamine or K6P can be biosynthesized in a first stage and then converted to aminoshikimate in a second stage of the enzymatic pathway.

Figure 4:
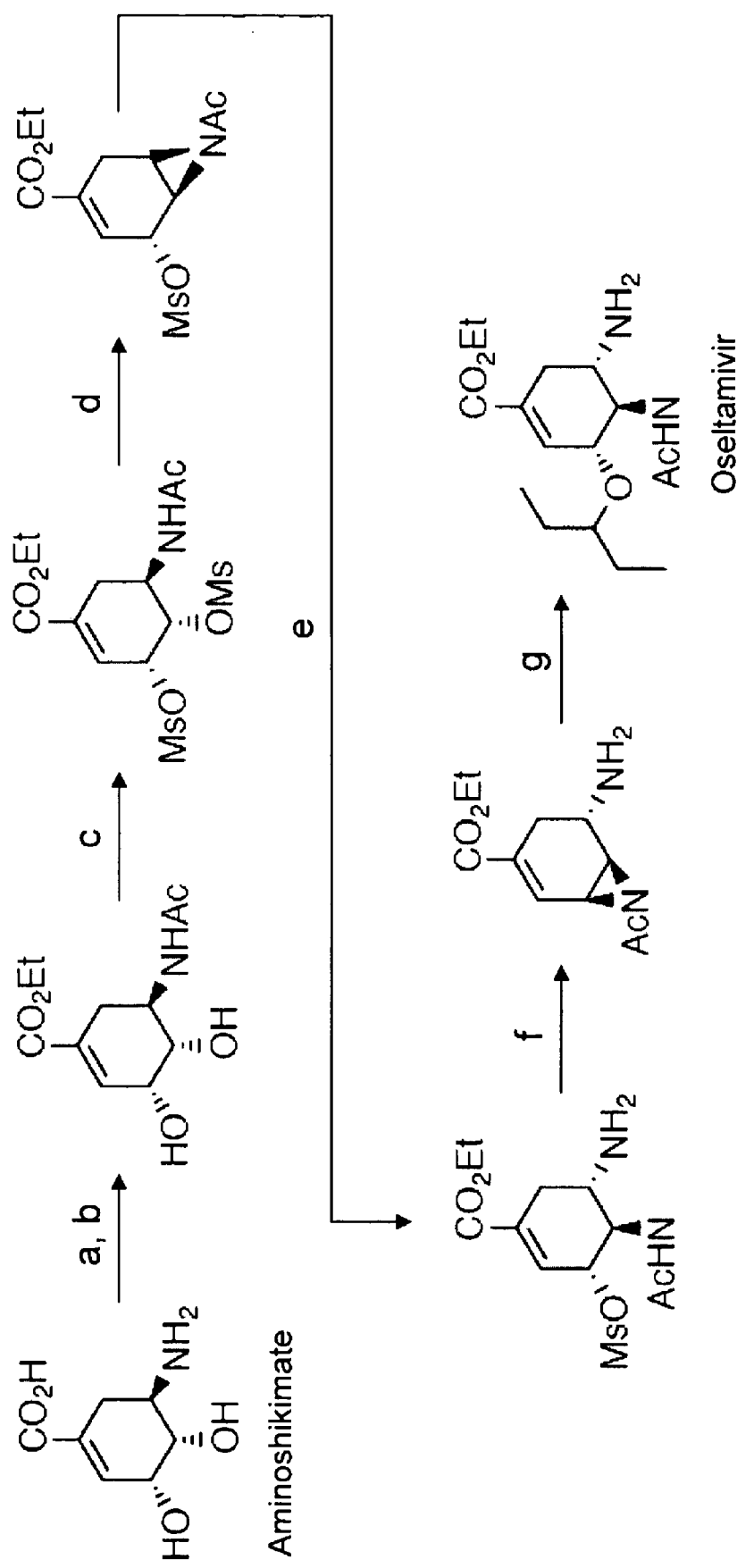

FIG. 4 illustrates one exemplary chemosynthetic pathway useful for conversion of aminoshikimic acid hereof to oseltamivir using the following reaction steps: (a) EtOH, H$^+$, i.e. acidified ethanol; (b) Ac$_2$O, H$^+$, i.e. acidified acetic anhydride; (c) MsCl, Et$_3$N, i.e. mesyl chloride in triethylamine; (d) KOt-Bu, t-BuOH, i.e. potassium t-butoxide in t-butyl alcohol; (e) NH$_3$; (f) KOt-Bu, t-BuOH; (g) (CH$_3$CH$_2$)CHO$^-$ K$^+$, (CH$_3$CH$_2$)CHOH, i.e. potassium pent-3-oxide in sec-n-amyl alcohol.

It should be noted that the figures set forth herein are intended to exemplify the general characteristics of methods among those of this invention, for the purpose of the description of such embodiments herein. These figures may not precisely reflect the characteristics of any given embodiment, and are not necessarily intended to define or limit specific embodiments within the scope of this invention.

BRIEF DESCRIPTION OF SEQUENCES

Sequences are presented in the accompanying Sequence Listing as shown in Table 1.

TABLE 1

Sequences Listed

| SID | Description |
|---|---|
| 1 | Coding sequence for 3-keto-D-glucose-6-phosphate (3KG6P) dehydrogenase (YhjJ) |
| 2 | 3KG6P dehydrogenase (YhjJ) amino acid sequence |
| 3 | Coding sequence for 3-keto-D-glucose-6-phosphate (3KG6P) transaminase (YhjL) |
| 4 | 3KG6P transaminase (YhjL) amino acid sequence |
| 5 | Coding sequence for kanosamine-6-phosphate (K6P) phosphatase (YhjK) |
| 6 | K6P phosphatase (YhjK) amino acid sequence |
| 7 | Coding sequence for 4-amino-3,4-dideoxy-D-arabino-heptulosonic acid 7-phosphate (aminoDAHP) synthase (RifH) |

TABLE 1-continued

Sequences Listed

| SID | Description |
|---|---|
| 8 | AminoDAHP synthase (RifH) amino acid sequence |
| 9 | Coding sequence for phosphoglucose isomerase (Pgi) |
| 10 | Phosphoglucose isomerase (PGI) amino acid sequence |
| 11 | Coding sequence for transketolase (TktA) |
| 12 | Transketolase (TktA) amino acid sequence |
| 13 | Coding sequence for 3-dehydroquinate (DHQ) synthase (AroB) |
| 14 | DHQ synthase (AroB) amino acid sequence |
| 15 | Coding sequence for 3-dehydroquinate (DHQ) dehydratase (AroD) |
| 16 | DHQ dehydratase (AroD) amino acid sequence |
| 17 | Coding sequence for shikimate dehydrogenase (AroE) |
| 18 | Shikimate dehydrogenase (AroE) amino acid sequence |
| 19 | Coding sequence for glucose kinase (Glk) |
| 20 | Glucose kinase (Glk) amino acid sequence |

DETAILED DESCRIPTION

The following definitions and non-limiting guidelines must be considered in reviewing the description of this invention set forth herein.

The headings (such as "Introduction" and "Summary,") and sub-headings (such as "Enzyme Systems") used herein are intended only for general organization of topics within the disclosure of the invention, and are not intended to limit the disclosure of the invention or any aspect thereof. In particular, subject matter disclosed in the "Introduction" may include aspects of technology within the scope of the invention, and may not constitute a recitation of prior art. Subject matter disclosed in the "Summary" is not an exhaustive or complete disclosure of the entire scope of the invention or any embodiments thereof.

The citation of references herein does not constitute an admission that those references are prior art or have any relevance to the patentability of the invention disclosed herein. Any discussion of the content of references cited in the Introduction is intended merely to provide a general summary of assertions made by the authors of the references, and does not constitute an admission as to the accuracy of the content of such references. All references cited in the Description section of this specification are hereby incorporated by reference in their entirety.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations of the stated features. Specific Examples are provided for illustrative purposes of how to make, use and practice the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the word "include," and its variants, is intended to be non-limiting, such that recitation of items in a list is not to the exclusion of other like items that may also be useful in the materials, compositions, and methods of this invention.

Various embodiments of the present invention involve biosynthetic production of aminoshikimic acid, i.e. 5-amino-5-deoxyshikimic acid. The biosynthetic route employs an improved enzymatic pathway that is capable of converting a simple carbon source to glucose-6-phosphate, followed by conversion thereof to kanosamine-6-phosphate, which is then converted to 1-imino-1-deoxy-D-erythrose-4-phosphate (iminoE4P); the iminoE4P is then reacted with phosphoenolpyruvate (PEP) to form 4-amino-3,4-dideoxy-D-arabino-heptulosonic acid 7-phosphate (aminoDAHP), which is then converted to aminoshikimate.

Figure 1:
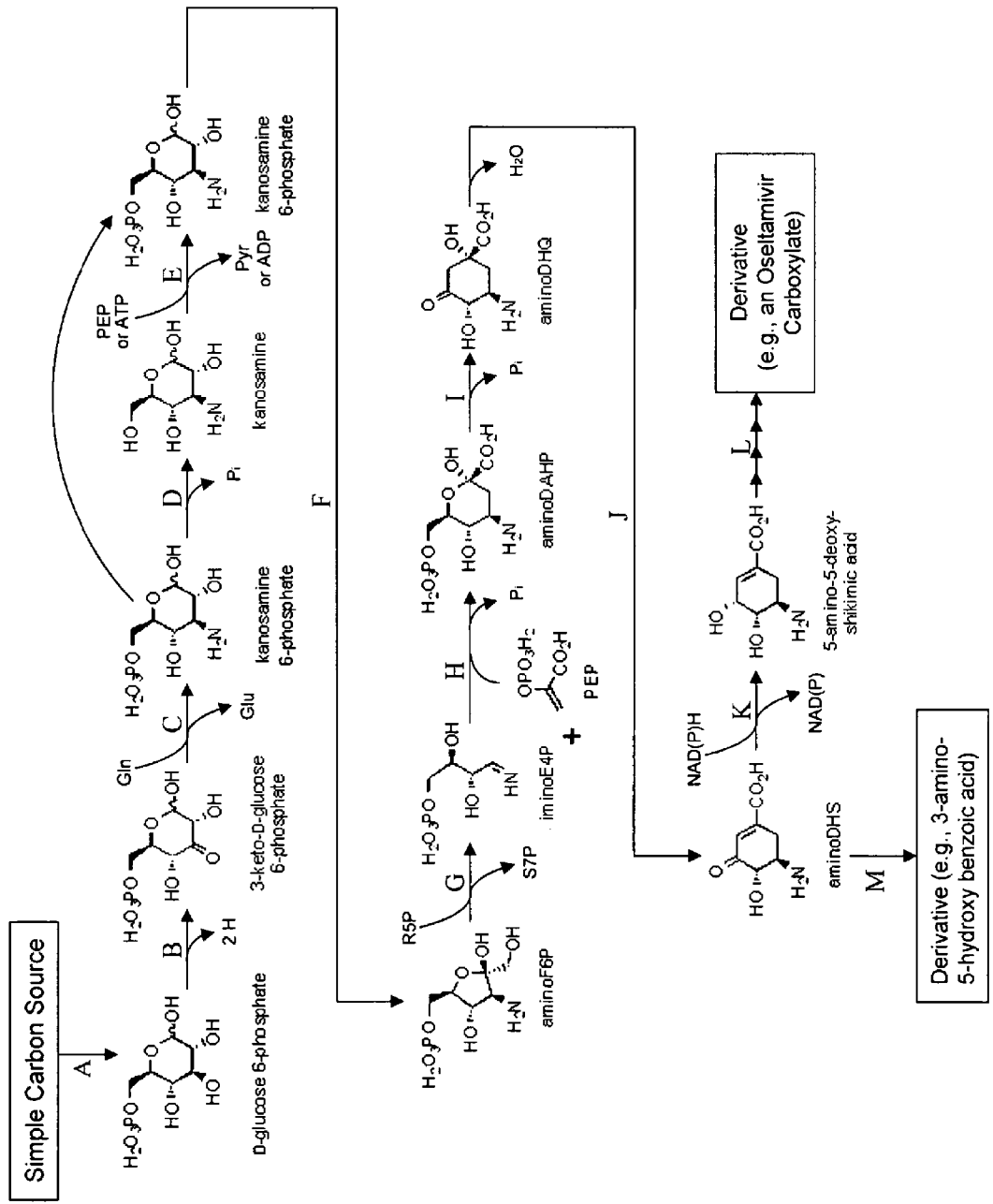
FIG. 1 illustrates one 9-step and one 11-step pathway for biosynthesis of 5-amino-5-deoxyshikimic acid, followed by conversion to a derivative thereof, e.g., an oseltamivir carboxylate; this Figure also shows a 3-step pathway for kanosamine production that involves steps B, C, and D, as well as a pathway for production of aminoDHS derivatives that involves step M.

Referring to FIG. 1, some embodiments of the present invention can comprise the following steps:

A. Conversion of a simple carbon source to glucose-6-phosphate (G6P);

B. Conversion of G6P to 3-keto-D-glucose-6-phosphate (3KG6P) by 3KG6P dehydrogenase (e.g., YhjJ, such as SEQ ID NO:2);

C. Conversion of 3KG6P to kanosamine-6-phosphate (K6P) by 3-keto-D-glucose-6-phosphate transaminase (e.g., YhjL, such as SEQ ID NO:4);

D. & E. Optional conversion of K6P to kanosamine by K6P phosphatase (e.g., YhjK, such as SEQ ID NO:6); and of such kanosamine to K6P by the phosphoenolpyruvate:carbohydrate phosphotransferase system (e.g., PTS; EC 2.7._._, such as that native to an expression host cell), using phosphoenolpyruvate (PEP), or by either glucose kinase (e.g., Glk; EC 2.7.1.2; such as SEQ ID NO:20) or kanosamine kinase (RifN; EC 2.7._; such as GenBank AAC01722, from AF040570), using ATP;

F. Conversion of K6P to 3-amino-3-deoxy-D-fructose-6-phosphate (aminoF6P) by phosphoglucose isomerase (e.g., Pgi; EC 5.3.1.9; such as SEQ ID NO:10);

G. Conversion of aminoF6P to 1-imino-1-deoxy-D-erythrose-4-phosphate (iminoE4P) by transketolase (e.g., TktA; EC 2.2.1.1, such as SEQ ID NO:12), with conversion of D-ribose-5-phosphate (R5P) to sedoheptulose-7-phosphate (S7P);

H. Conversion of iminoE4P to 4-amino-3,4-dideoxy-D-arabino-heptulosonic acid 7-phosphate (aminoDAHP) by aminoDAHP synthase (e.g., RifH, such as SEQ ID NO:8), using PEP;

I. Conversion of aminoDAHP to 5-amino-5-deoxy-3-dehydroquinic acid (aminoDHQ) by 3-dehydroquinate (DHQ) synthase (e.g., AroB; EC 4.2.3.4, formerly EC 4.6.1.3; such as SEQ ID NO:14) or by aminoDHQ synthase (e.g., RifG, such as GenBank AAC01717, from AF040570; AnsA, such as GenBank AAD31832, from AH007725; or NapC, such as GenBank AAD31825, from AF131877);

J. Conversion of aminoDHQ to 5-amino-5-deoxy-3-dehydroshikimic acid (aminoDHS) by DHQ dehydratase (e.g., AroD; EC 4.2.1.10, such as SEQ ID NO:16) or by aminoDHQ dehydratase (e.g., RifJ, such as GenBank AAS07762, from AF040570; or AnsE, such as GenBank AAD31834, from AH007725);

K. Conversion of aminoDHS to 5-amino-5-deoxyshikimic acid (aminoshikimic acid) by shikimate dehydrogenase (e.g., AroE; EC 1.1.1.25, such as SEQ ID NO:18) using NADPH, by quinate/shikimate dehydrogenase. (e.g., YdiB; EC 1.1.1.282; such as GenBank P0A6D5, from NC_000913) using either NADH or NADPH, or by aminoquinate/aminoshikimate dehydrogenase (e.g., RifI, such as GenBank AAC01719, from AF040570) using NADPH; and L. Conversion of aminoshikimic acid to a derivative or derivatives, such as by multi-step chemosynthetic conversion of aminoshikimate to an oseltamivir carboxylate.

Various embodiments of the present invention involve biosynthetic production of kanosamine. Referring to FIG. 1, some embodiments of the present invention can comprise the following steps:

A. Conversion of a simple carbon source to glucose-6-phosphate (G6P);

B. Conversion of G6P to 3-keto-D-glucose-6-phosphate (3KG6P) by 3KG6P dehydrogenase (e.g., YhjJ, such as SEQ ID NO:2);

C. Conversion of 3KG6P to kanosamine-6-phosphate (K6P) by 3-keto-D-glucose-6-phosphate transaminase (e.g., YhjL, such as SEQ ID NO:4); and D. Conversion of K6P to kanosamine by K6P phosphatase (e.g., YhjK, such as SEQ ID NO:6).

In some embodiments where glucose-6-phosphate is already present, a process for biosynthetic kanosamine production can be performed by use of a process comprising steps B, C, and D, without requiring step A.

This process for biosynthesis of aminoshikimate is anabolic, i.e. capable of using simple carbon sources as starting materials; thus, even though, e.g., step G is a catabolism, the overall process is anabolic. As indicated in step A, a simple carbon source may be used as the starting material for synthesis of G6P. A wide variety of different carbon sources may be used, including organic and inorganic carbon sources, provided that the host cell or enzyme system is capable of converting the carbon source to G6P, if the carbon source is other than G6P.

Where the carbon source comprises a biomolecule-type carbon compound, the carbon compound can be a primary metabolite-type compound. Examples of primary metabolite-type compounds include any of the, e.g., C1-C18: fatty acids, waxes, mono-, di-, and tri-glycerides; polyols; aliphatic hydroxy acids; phospholipids; phosphoacids; monosaccharides (e.g., trioses, tetroses, pentoses, hexoses, heptoses, and the like); amino acids; and nucleotides; and hydrolysable homo- and hetero-oligomers (i.e., including -dimers) and -polymers obtainable from such compounds; and biologically activated forms of such compounds (e.g., acetyl-CoA). Biomolecule-type compounds may be of any origin, whether biological or synthetic. Other useful compounds include any small or non-complex organic compounds, i.e. generally C1-C18, aliphatic cycloaliphatic, and aromatic compounds, and the like, of any source, having a preferred monomeric complexity of 4 or fewer carbon-carbon branch points per 18 carbon atoms, e.g.: C1-C18 aliphatic hydrocarbons and their mono- and poly-acids, -alcohols, -amines, -carbonyls; and hydrolysable homo- and hetero-oligomers and -polymers formed therefrom.

Carbon sources comprising such small/non-complex organic(s), and/or primary metabolite-type compound(s), without substantial concentrations of (and preferably less than 10%-of-carbon-by-weight concentrations of) secondary metabolites or of larger-monomer-type or complex organic compounds are also referred to herein as "simple" carbon sources. As used herein, secondary metabolites include, e.g.: alkaloids; coumarins; polyketides; terpenoids, isoprenoids, sterols, steroids, and prostaglandins; catecholamines; porphyrins; xanthones; flavonoids; phenylpropanoids and phenolics (including, e.g., benzenoids and polyphenolics); and the like. Large or complex organic compounds are aliphatic, cycloaliphatic, and aromatic compounds, and the like, that have a monomeric compound size above C18 and/or a monomeric compound complexity above 4 carbon-carbon branch points per 18 carbon atoms.

In some embodiments, a carbon source can be a simple carbon source. Such simple carbon sources can contain from 0% to about 5%, more preferably from 0% to about 2%, or 0% to about 1%, or 0% to about 0.5%, or preferably about 0% by weight secondary metabolites and larger or complex organics; or can be free or at least substantially free of secondary metabolites and larger/complex organics. In some embodiments, a simple carbon source can comprise primary metabolite-type compound(s). Examples of useful primary metabolite-type compound(s) for use herein include: saccharides, e.g., mono- and/or di-saccharides; and polyols. Glucose, xylose, and arabinose are examples of a monosaccharide for use in a carbon source herein; glycerol is one example of a polyol therefore. In one embodiment hereof, a carbon source can comprise glucose, xylose, and/or arabinose, and such a carbon source can be employed throughout both the exponential growth phase and the maintenance phase of a host cell culture. In some embodiments, a combination of a monosaccharide(s) (e.g., glucose, xylose, and/or arabinose) and glycerol can be used, e.g., a 1:1 or 2:1 weight ratio; some embodiments can use such a combination as the carbon source during the maintenance phase, with monosaccharide(s) (without glycerol) being used during the exponential growth phase. Conversion of a simple carbon source to glucose-6-phosphate may be obtained, e.g., by gluconeogenesis, glucose phosphorylation, or conversion of saccharides or saccharols to G6P.

Steps D and E may be eliminated in some embodiments, including: those in which kanosamine-6-phosphate (K6P) is converted to aminoF6P at such a rate that no substantial pool of K6P accumulates, e.g., wherein phosphoglucose isomerase is overexpressed; those in which the host cells employed contain no, or at least no essential, glucosamine-6-phosphate synthase; those in which the host cells employed contain a glucosamine-6-phosphate synthase that is insensitive to inhibition by K6P; or those in which K6P is biosynthetically obtained in a first step, and then supplied to another organism or system that is to covert it to one of the downstream products, e.g., any of the sequential products from aminoF6P to aminoshikimate.

Where steps D and E are included, a host cell can supply a phosphoenolpyruvate:carbohydrate phosphotransferase system, which can react phosphoenolpyruvate (PEP) with kanosamine to obtain K6P, with a pyruvate by-product. In some embodiments, a host cell can be one that lacks such a PTS, either naturally or by, e.g., gene manipulation, but that retains or is transformed to contain either a glucose kinase or a kanosamine kinase, both of which use ATP to provide the same phosphate functionality for K6P. J. L. Baez et al., *Biotechnol. Bioeng.* 73(6):530-35 (Jun. 20, 2001).

After biosynthesis of aminoshikimate by an enzymatic pathway hereof, the aminoshikimate can be recovered from the cells and/or culture medium, for example, by use of a cation exchange column. The aminoshikimate can then be further treated, either bio- or chemo-synthetically, or both. In some embodiments, a chemosynthetic treatment will be applied to form a derivative or derivatives thereof. Oseltamivir carboxylates can be derived thereby.

Enzyme Systems

Use of phrases such as "recombinant enzyme system" and "isolated or recombinant enzyme system" do not imply that all enzymes of the systems must be recombinant or isolated, but only that at least one member of the system is recombinant or isolated.

Systems for Aminoshikimate Biosynthesis

In some embodiments of an enzyme system according to the present invention, the enzyme system can comprise: (1) a 3-keto-D-glucose-6-phosphate (3KG6P) dehydrogenase, (2) a 3-keto-D-glucose-6-phosphate (3KG6P) transaminase, and (3) a 4-amino-3,4-dideoxy-D-arabino-heptulosonic acid 7-phosphate (aminoDAHP) synthase. Though not bound by theory, it is believed that this combination of enzyme functionalities has not previously been prepared.

The enzyme system can contain, in addition to these three: (4) a phosphoglucose isomerase (Pgi); (5) a transketolase (TktA); (6) a 3-dehydroquinate (DHQ) synthase or a 5-amino-3-dehydroquinate (aminoDHQ) synthase; (7) a 3-dehydroquinate (DHQ) dehydratase or a 5-amino-3-dehydroquinate (aminoDHQ) dehydratase; and (8) a shikimate dehydrogenase, a quinate/shikimate dehydrogenase, or an aminoquinate/aminoshikimate dehydrogenase. Where all 8 of these enzymes are present in a cell that requires N-acetylglucosamine synthesis, performed by a pathway involving glucosamine-6-phosphate synthase, the culture medium can be supplemented with N-acetylglucosamine in order to decrease inhibition of the essential enzyme.

In some embodiments, an enzyme system according to the present invention can further comprise, in addition to the above 8, both: (9) a kanosamine-6-phosphate (K6P) phosphatase; and (10) a phosphoenolpyruvate:carbohydrate phosphotransferase system, a glucose kinase (Glk), or a kanosamine kinase.

In some embodiments, an enzyme system according to the present invention can further comprise (11) an enzyme or enzymes capable of producing glucose-6-phosphate from a carbon source. Yet, in embodiments in which 6GP is provided in or as the carbon source, these enzymes need not be present in the enzyme system. Other enzymes, non-enzymatic proteins, and factors may also be present with an enzyme system hereof. For example, multiple copies of any one of the genes (i.e. or operons) encoding enzymes of an enzymes system hereof may be used so that additional copies of those enzymes are present; a repressor protein, and its encoding gene, may be present.

Systems for Kanosamine Biosynthesis

The present invention further provides improved methods and enzymatic pathways for biosynthesis of kanosamine. Kanosamine, or 3-amino-3-deoxy-D-glucose (CAS No. 576-44-3) is an intermediate in a process for production of aminoshikimate hereby, which can, in some embodiments, be converted to a derivative, such as an oseltamivir carboxylate. Yet, kanosamine itself is useful: as an antiparasitic agent against oomycetes, such as *Phytophthora* and *Pythium* plant pathogens; as an antifungal agent against various plant and animal pathogens, such as *Candida, Fusarium, Saccharomyces, Ustilago*, and *Verticillium*; and as an antibiotic agent against, e.g., *Staphylococcus, Erwinia*, and *Cytophaga*. For example, in fungi, imported kanosamine is converted to kanosamine-6-phosphate, which acts as an inhibitor of fungal glucosamine-6-phosphate synthase.

In some embodiments, a biosynthetic kanosamine enzyme system can include (1) at least one 3-keto-D-glucose-6-phosphate (3KG6P) dehydrogenase, (2) at least one 3-keto-D-glucose-6-phosphate (3KG6P) transaminase, and (3) at least one K6P phosphatase, present with a source of glucose-6-phosphate, for example, present in a cell capable of converting a carbon source to G6P. These three enzymes are, respectively, capable of catalyzing the conversion of glucose-6-phosphate (G6P) to 3-keto-D-glucose-6-phosphate (3KG6P), 3KG6P to kanosamine-6-phosphate (K6P), and K6P to kanosamine.

In some embodiments, the kanosamine so produced can be isolated for use. In some embodiments, the recombinant expression host cells containing kanosamine can be dried, lyophilized, or otherwise preserved for use in an agricultural, horticultural, veterinary, or other environmental application.

In some embodiments, a recombinant microbial expression host can be a cell capable of forming a protective spore or cyst, such as a bacterial protective spore, fungal spore, or protist cyst. Where such a microbe is employed, the host cell can be grown until such a protective stage is obtained and the resulting spores or cysts can then be used in agricultural, horticultural, veterinary, or other environmental applications, such as in the form of a dust or spray applied to plants or seeds, or to soil or other growth media: the spores or cysts can thereafter germinate to provide a live, microbial source of kanosamine production, e.g., on a treated plant. Representative examples of microbial host cells useful for production of such spores or cysts include, e.g., *Bacillus, Pythium*, and *Trichoderma*; microbial strains that are non-pathogenic for the subject to be treated can be used.

Similarly, in some embodiments, live-microbial-cells of recombinant host cells hereof, which are capable of kanosamine synthesis, can be applied directly to such subjects. Representative examples of microbes useful for such live-microbial-cell embodiments include any of the above spore- or cyst-forming microbes, as well as other environmentally-compatible microbes, such as environmentally-compatible bacteria of the genera, e.g., *Acinetobacter, Agrobacterium, Alcaligenes, Arthrobacter, Azospirillum, Burkholderia, Enterobacter, Erwinia, Flavobacterium, Pseudomonas, Rhizobium*, and *Serratia*. Likewise, those microbial strains that are non-pathogenic for the subject to be treated can be used.

Nucleic Acids and Recombinant Cells

Novel nucleic acid encoding an enzyme system according to the present invention likewise can comprise genes (i.e. or operons) encoding at least the above combination of enzymes (1), (2), and (3): 3KG6P dehydrogenase, 3KG6P transaminase, and aminoDAHP synthase. Such novel nucleic acid may comprise genes (i.e. or operons) encoding at least enzymes (1) to (8), listed above, or at least the above-listed enzymes (1) to (10), or at least the above-listed enzymes (1) to (11). As further discussed hereinbelow, the genes or operons encoding enzymes of a pathway according to an embodiment of the present invention, may be constitutively expressed, or under the control of a regulatable promoter.

Examples of useful promoters include, e.g., Ptac, Plac, Ptrc, Ptrp, PT7, PL, and PR. These may be operatively attached to the coding sequences hereof by any techniques known in the art. Further regulatory regions to be included are transcription and translation termination signals and ribosome binding sites. Coding sequences hereof may be expressed as fusions with terminal nucleic acid encoding terminal peptide targeting signals, peptide labels, or other polypeptide fusion partners. The nucleic acid may be provided in the form of a multi-enzyme construct. Examples of such multi-enzyme constructs can include multiple coding sequences (i.e. more than one coding sequence) encoding a plurality (i.e. more than one) of enzymes to be expressed as part of a single polypeptide molecule, where the coding sequences are under the control of a single promoter. In some embodiments, each of the enzymes to be expressed in a given embodiment will be expressed from a coding sequence that is under the control of a promoter that is dedicated to that coding sequence and that can be the same or a different promoter from those of other coding sequences for the enzyme pathway, e.g., each coding sequence can be under the control of a separate copy of Ptac.

In some embodiments, nucleic acid can be provided in the form of a cloning or expression vector, such as a plasmid, cosmid, plasposon, viral genome, or artificial chromosome, e.g., a YAC or BAC. In some embodiments, all genes encoding enzymes in a pathway according to the present invention can be located on the same vector, or can be situated among two or more vectors. In some embodiments, all genes encoding enzymes in a pathway according to the present invention can be located in chromosomal DNA of a host cell, or can be situated among chromosomal and extrachromosomal DNA in the host cell.

Cells that can be used as expression host cells are described below. Cloning hosts include the same range of host cells. Host cells may be transformed by any technique known in the art. In some embodiments, bacterial or fungal cells can be used. Molecular biological techniques for forming nucleic acid constructs and for transforming cells for cloning or expression purposes are well known in the art. For example, techniques described, e.g., in J. Sambrook, E. F. Fritsch & T. Maniatis, *Molecular Cloning: A Laboratory Manual* (2d ed., 1989) (Cold Spring Harbor Laboratory Press) can be used.

Enzymes System Formats

The biosynthetic process can be operated in a variety of different formats. An enzymatic pathway according to some embodiments may be present in a single organism or jointly among two or more cells or organisms. In some embodiments, a first cell or organism can contain enzymes for performing some of the steps, e.g., steps B through C or D and optionally step A, and a second cell or organism contain the other enzymes for performing the remainder of the pathway, e.g., steps E through K. In some embodiments, a cell or organism containing enzymes for performing steps B, C, and D, and optionally step A, can be employed to produce kanosamine. In some embodiments, the cells can comprise cultured cells from a multicellular organism, whether differentiated or dedifferentiated; in some embodiments, the organisms can be single-cell organisms. In some embodiments, in which the cells are walled cells, the cells can comprise protoplasts or spheroplasts or both.

Thus useful cells include animal cells, plant cells, fungal cells (including yeast cells), bacterial cells, archaeal cells, protist cells, and the like. In some embodiments, the cells can comprise plant cells, fungal cells, bacterial cells, or algal cells. In some embodiments, the cells can comprise fungal cells or bacterial cells. Useful bacterial cells include, e.g., eubacteria, such as the proteobacteria. In some embodiments, the proteobacteria can be gamma proteobacteria, such as an enterobacterium, e.g., *Escherichia coli*, or a pseudomonad, e.g., *Pseudomonas fluorescens. E. coli* strain W3110 may be obtained as ATCC No. 27325 (American Type Culture Collection, Manassas, Va., USA); and *P. fluorescens* strain Pf-5 may be obtained as ATCC No. BAA-477.

The process can be operated in the form of an immobilized enzyme bioreactor(s), or in the form of a cell lysate(s) or mixture of cell lysates. Two-stage processes can also be used in which an intermediate, e.g., kanosamine or kanosamine-6-phosphate, can be formed in a first bioreactor, lysate, cell, or organism, which intermediate can then be provided to a second stage organism, cell, lysate, or bioreactor for completion of the biosynthesis.

In some embodiments, host cells used can be any that contain a functioning shikimate synthesis pathway, in which case the Aro-type enzymes of steps I, J, and K can be supplied by the host cell's native complement of biocatalysts. In such cells, for example in bacterial cells having a functioning shikimate synthesis pathway, the host cell can be transformed with either or both of host-cell-expressible DNA encoding: (1) a step B and a step C enzyme, e.g., .YhiJ and YhiL, and in some embodiments also a step D enzyme, e.g., YhiK; and (2) a step H enzyme, e.g., RifH.

In some embodiments, a host cell can be constructed by transforming it with expressible DNA encoding at least one of the steps B through K enzymes (referring to FIG. 1), where the host cell provides the remaining enzymes of the pathway. In some embodiments, all 8 or 10 of the biosynthetic activities may be provided by transforming the host cell with as many host-cell-expressible genes.

Fermentation Conditions

A culture of whole cells used in a method for producing aminoshikimate according some embodiments of the present invention can utilize conditions that are permissive for cell growth and those that permit the cultured cells to produce anabolic aminoshikimate. As used herein, the terms culturing and fermentation are used interchangeably, and fermentative metabolism is not required herein. In some embodiments, some (e.g., yhjJ, yhjL, rifH, and optionally yhjK) or all of the aminoshikimate pathway enzymes can be expressed throughout the cell culture period, e.g., constitutively; yet, in some embodiments, it is desirable to begin expressing some (e.g., yhjJ, yhjL, rifH, and optionally yhjK) or all of the pathway enzymes only near the end of the exponential growth phase (EGP). The same holds true for some embodiments in which yhjJ, yhjL, and yhjK are to be expressed for kanosamine production. Where a later expression is desired, a pathway enzyme(s) coding sequence(s) under the control of a regulated promoter generally can be activated or derepressed when about 70 to 100%, or when about 70 to about 90%, or when about 70 to about 80% of EGP has elapsed. Examples of promoters useful for this purpose include the tac, T5, and T7 promoters; induction may be made using lactose or a gratuitous inducer such as IPTG (isopropyl-beta-D-thiogalactopyranoside).

In some embodiments hereof, a recombinant microbial cell, such as a recombinant bacterial host cell can be used as a whole cell biocatalyst herein. Examples of bacteria useful for this purpose include proteobacteria; examples of useful proteobacteria include the gamma proteobacteria, such as enterobacteria and pseudomonads; *Escherichia* spp., such as *E. coli*, and *Pseudomonas* spp., such as *P. fluorescens*, are useful examples of these. Host cells can be used that lack or have been treated to decrease or eliminate protease activities that would be capable of degrading the aminoshikimate synthesis pathway enzymes. In bacteria, Lon and OmpT are two examples of proteases that can be advantageous absent, decreased, or eliminated, e.g., by mutation.

In the case of *E. coli*, fermentation temperatures can be from about 20 to about 37° C., or from about 25 to about 37° C., or about 30 to about 37° C. In the case of *P. fluorescens*, fermentation temperatures can be from about 20 to about 30° C., or from about 27 to about 30° C., or from about 24 to about 27° C.

Fermentations can be performed in any format, whether batch, fed batch, continuous, and the like. In some embodiments, an extractive fermentation mode can be employed, wherein a cation exchange medium can be used to recover aminoshikimate from the culture medium during fermentation. In such an embodiment the cation exchange medium can be applied in any useful mode known in the art, e.g.: cation exchange beads can be mixed with and then recovered from the culture; a cation exchange column can be used to process the fermentation medium during fermentation, and the resulting aminoshikimate-depleted effluent can be returned to the fermentation tank; a cation exchange membrane may be employed; and so forth. Similarly, after any fermentation, whether extractive or non-extractive, or any other enzymatic synthesis of aminoshikimate according to an embodiment hereof, has been performed, resulting cells can be lysed and any resulting lysate and/or remaining culture media can be contacted with a cation exchange medium for recovery of aminoshikimate. Other useful aminoshikimate separation or fractionation techniques known in the art can be used alternatively or in addition. Similarly, fermentations for kanosamine production can utilize any such fermentation mode and kanosamine by be recovered using an ion exchange medium or any other useful recovery technique known in the art.

Derivatives

In some embodiments, aminoshikimate, kanosamine, or an intermediate between kanosamine and aminoshikimate, produced by a biosynthetic process hereof can be converted to derivative(s) thereof. In some embodiments, biosynthetic kanosamine hereof, by conversion to its aminoDSH derivative, or biosynthetic aminoshikimate hereof, by conversion to its aminoDHS precursor, can be converted to aminoDHS derivative(s), of which an exemplary class includes the 3-hydroxy-5-amino benzoic acid derivatives, i.e. the 3-amino-5-hydroxy benzoic acid (AHBA) derivatives. AminoDHS can be converted to AHBA as described, e.g., by R. J. Cox, "Biosynthesis," in *Annu. Rep. Prog. Chem., Sect. B (Organic Chemistry)* 94:187-206 (1998), at p. 202 (Royal Society of Chemistry; RSC Publ., Cambridge, GB; DOI: 10.1039/oc094187). AHBA is useful as a precursor of the ansamycin and mitomycin antibiotics, and it is also useful in combinatorial synthesis for development of pharmaceuticals, e.g., see Dankwardt et al., *Molec. Divers.* 1(2):113-20 (February 1996).

In some embodiments, an exemplary class of aminoshikimate derivatives includes the 4,5-diamino shikimic acid derivatives, i.e. the 4,5-diamino-4,5-dideoxyshikimic acid derivatives; these and their salts are useful as viral neuraminidase inhibitors. See, e.g., U.S. Pat. No. 6,403,824 to Abrecht et al. and U.S. Pat. No. 6,462,226 to Mair. An exemplary subclass of 4,5-diamino shikimic acid derivatives includes the oseltamivir carboxylates.

Oseltamivir carboxylates are potent inhibitors of viral neuraminidases and are useful as antiviral agents. As used herein, oseltamivir carboxylates include oseltamivir carboxylate itself, as well as esters, salts, and complexes thereof, which in some embodiments can be pharmaceutically acceptable salts, esters, and complexes. Oseltamivir carboxylate is an isomer of 3-O-(pentan-3-yl)-4-acetylamino-5-amino-4,5-dideoxyshikimic acid, and has the formula (3R,4R,5S)-4-acetylamino-5-amino-3-(1-ethylpropoxy)-1-cyclohexene-1-carboxylic acid, and the CAS Registry No. 187227-45-8.

Exemplary oseltamivir carboxylate esters include C1 to C18 aliphatic esters; in some embodiments, these can be C1 to C4 esters, or C2 esters. The C2 (i.e. ethyl) ester of oseltamivir carboxylate is referred to as "oseltamivir" or "oseltamivir free base," which has the formula (3R,4R,5S)-4-acetylamino-5-amino-3-(1-ethylpropoxy)-1-cyclohexene-1-carboxylic acid, ethyl ester, and is assigned CAS Registry No. 196618-13-0.

Exemplary oseltamivir salts and complexes include phosphoxy acid, sulfoxy acid, nitroxy acid, and carboxy acid salts and complexes; in some embodiments, the salts and complexes can be phosphate salts and phosphoric acid complexes. In some embodiments, a member of the oseltamivir carboxylates can be both an ester, and a salt or complex, of oseltamivir carboxylate; in some embodiments, one such member can be oseltamivir phosphate, which has CAS Registry No. 204255-11-8.

Oseltamivir phosphate, the active ingredient in TAMIFLU, has the formula (3R,4R,5S)-4-acetylamino-5-amino-3-(1-ethylpropoxy)-1-cyclohexene-1-carboxylic acid, ethyl ester, phosphate (1:1), and can be considered as either a complex or a salt formed between phosphoric acid and the 5-amino group of oseltamivir, i.e. as a 5-N-salt or 5-N-complex. Oseltamivir free base and oseltamivir phosphate are oseltamivir carboxylate ethyl ester pro-drugs that, following administration to humans or, e.g., vertebrate animals, are deesterified in vivo to form the viral-neuraminidase inhibitor, oseltamivir carboxylate.

One of ordinary skill in the organic chemistry art will recognize many useful chemosynthetic routes for converting aminoshikimate (aminoSA) to a 4,5-diamino shikimic acid derivative, such as an oseltamivir carboxylate, e.g., oseltamivir or oseltamivir phosphate.

In some embodiments, as in the case of oseltamivirs and similar compounds, desired outcomes of transforming aminoSA thereto can include: converting the 1-carboxyl group to a 1-carboxyl ester, e.g., the ethyl ester; converting the 3-(R)-hydroxy group to a 3-(R)-ether group, e.g., the pentan-3-yl ether; converting the 4-(S)-hydroxy group to a 4-(R)-acylamino group, e.g., the acetylamine; and converting the 5-(R)-amino group to a 5-(S)-amino group. These conversions can be performed in a variety of orders.

For example, in some embodiments, aminoSA can be treated by: (1) protecting the aminoSA 5-amino group by reaction with benzaldehyde to form a 5-N-imine; (2) esterifying the acid group with ethanol; (3) ketalizing the 3- and 4-hydroxy groups using diethyl ketone and p-toluenesulfonic acid, followed by ketal reduction to obtain a 3-O-(pentan-3-yl) ether while restoring the 4-hydroxy group, in a proportion of the molecules of the resulting mixture of isomers, and optionally recovering the isomer having the desired stereochemistry either at this point or later in the process; (4) mesylating the 4-hydroxy group with mesyl chloride in triethylamine, followed by transimination with allylamine and then aziridination to obtain a (fused) 4,5-aziridine ring, while also removing the imine partner from the 5-N; (5) opening the 4,5-aziridine ring with allylamine, followed by transimination and then acid hydrolysis to obtain a 4-amino group, while creating a 5-N-allyl substituent; (6) acetylating the 4-amino group to obtain a 4-acetylamino group; and (7) deallylating the 5-N-allyl to restore a 5-amino group, and forming a phosphate salt (or complex) therewith, to thereby obtain oseltamivir phosphate.

In some embodiments, aminoshikimate can be chemosynthetically converted to oseltamivir by operation of a process such as that illustrated in FIG. 4. Such a process can comprise: (a) esterifying the acid group with acidified ethanol, and (b) acetylating the 5-amino group with acidified acetic anhydride; (c) mesylating the 3- and 4-hydroxy groups with mesyl chloride (i.e. methanesulfonyl chloride) in triethylamine; (d) aziridinating the 4-O-mesyl and 5-acetylamine groups with potassium t-butoxide in t-butyl alcohol to form a fused 4,5-aziridine ring in which the nitrogen remains acetylated; (e) opening the resulting 4,5-(acetyl)aziridine ring with ammonia to restore a 5-amino group, while creating a 4-acetylamine group; (f) aziridinating the 3-O-mesyl and 4-acetylamine groups with potassium t-butoxide in t-butyl alcohol to form a fused 3,4-aziridine ring in which the nitrogen remains acetylated; and (g) opening the resulting 3,4-(acetyl)aziridine ring with the potassium pentoxide, $(CH_3CH_2)CHO^-K^+$, in sec-n- amyl alcohol, $(CH_3CH_2)CHOH$, to restore a 4-acetylamine group while creating a 3-O-(pentan-3-yl) group, thereby obtaining oseltamivir.

Treatment of oseltamivir with an acid, such as a pharmaceutically acceptable acid, e.g., phosphoric acid, can be performed to obtain oseltamivir additional salts, such as oseltamivir phosphate. Aminoshikimic acid produced according to an anabolic biosynthetic process hereof can be converted thereby to oseltamivir and/or to oseltamivir phosphate for use, e.g., in viral neuraminidase inhibitory compositions and treatments.

Other useful 4,5-diamino shikimic acid derivatives include: those having other hydrocarbyl groups, which are other than pentan-3-yl, as 3-O ether partners, e.g., C1-C8, or C1-C6 hydrocarbyl; those having other acyl groups, which are other than acetyl, as 4-N acylamino partners, e.g., C1-C12, or C1-C6 acyl; and/or those having other hydrocarbyl groups (obtainable from alcohols), which are other than ethyl, as 1-carboxy ester partners, e.g., C1-C12, or C1-C6 hydrocarbyl. In some embodiments, the 3-O-ether partner, the 4-N acylamino partner(s), and the 1-carboxy ester partner, respectively can be C18 or smaller hydrocarbyl, C18 or smaller acyl, or C18 or smaller hydrocarbyl. In some embodiments, non-aromatic hydrocarbyl and non-aromatic acyl partners can be used at all. Further derivatives and further examples of chemistries that can be used in forming 4,5-diamino shikimic acid derivatives of aminoSA herein include those described in C. U. Kim et al., *J. Am. Chem. Soc.* 119 (4):681-90 (1997).

Useful derivatives of aminoSA include, but are not limited to such 4,5-diamino shikimic acid derivatives. In addition, in some embodiments, an aminoshikimate starting material for production of aminoshikimate derivatives by any of the above chemosynthetic processes, can be obtained from any source. In some such embodiments, the aminoSA can be obtained by operation of other biosynthetic pathways, by operation of chemosynthetic pathways, or by a combination of such synthesis types. Yet, in some embodiments, an aminoshikimate starting material can comprise aminoshikimate produce by a biosynthetic process according to the present invention.

Compositions

Kanosamine, oseltamivir carboxylates, or other pharmaceutically useful derivatives produced from kanosamine or aminoshikimate according to some embodiments of the present invention can be formulated for human or veterinary administration. For example, antiviral pharmaceutical compositions can be prepared that contain at least one oseltamivir carboxylate derivative of aminoshikimate synthesized in an embodiment of the present invention. Techniques useful for preparing compositions for administration to human or animal subjects are commonly known in the art, and any such techniques may be employed in preparing a composition according to an embodiment of the present invention. See, e.g., A R Gennaro, Remington's Pharmaceutical Sciences (1990) (18th ed.; Mack Publishing Co.), hereby incorporated by reference.

The composition comprising the oseltamivir carboxylate or other derivative can be prepared in any useful format, such as a parenteral tablet, capsule, solution, powder, and the like. The formulation may contain any one or more of: fillers or binders, such as saccharide or saccharide alcohol fillers or binders (e.g., starch, sorbitol) or polyvinylpyrrolidone fillers or binders (e.g., povidone K 30); disintegrants, such as cellulose alkyl ethers (e.g. croscarmellose sodium); smoothing or processing agents, such as talc; lubricants, such as fatty acids and fatty acid esters (e.g., sodium stearyl fumarate); drug release modifying agents, such as gums (e.g., xanthan gum); salts or buffers, such as sodium citrate; stabilizing agents or preservatives, such as sodium benzoate; taste-enhancing agents, such as sweeteners (e.g., saccharin) and flavorings; colorants or whiteners, such as titanium dioxide; and so forth.

Similarly, kanosamine biosynthesized in various embodiments hereof can be formulated for human, veterinary, agricultural, horticultural, or other environmental administration.

Kits

In some embodiments of the present invention, a kit can be provided that contains isolated or recombinant nucleic acid comprising at least one aminoshikimate pathway gene hereof, or at least yhjJ, yhjL, and rifH, with instructions for using the nucleic acid to construct a transformant host cell capable of synthesizing aminoshikimate by operation of an enzymatic pathway hereof. In some embodiments of the present invention, a kit can be provided that contains isolated or recombinant nucleic acid comprising at least one kanosamine pathway gene hereof, or at least yhjJ, yhjL, and YhjK, with instructions for using the nucleic acid to construct a transformant host cell capable of synthesizing kanosamine by operation of an enzymatic pathway hereof.

In some embodiments, a kit can be provided that contains at least one transformed cell containing nucleic acid encoding at least one recombinant enzyme of an aminoshikimate or kanosamine synthesis pathway hereof, with instructions for using the cell to biosynthesize aminoshikimate or kanosamine thereby. In some embodiments, a kit can be provided that contains at least one isolated or recombinant enzyme of an aminoshikimate or kanosamine synthesis pathway hereof, with instructions for using the enzyme(s) to biosynthesize aminoshikimate or kanosamine thereby. The kits may further contain buffers, salts, e.g., $MgCl_2$; controls; reporter genes; stabilizing agents, e.g., polyethyleneglycols (PEGs), saccharides such as trehalose or sucrose, PEG-saccharides such as PEG-dextran, and the like; additional instructions and/or reagents for converting the aminoshikimate or kanosamine to a useful derivative thereof; and the like. The biomolecules or cells provided in the kit may be provided lyophilized, frozen, or in any other convenient form.

The present invention is further illustrated through the following non-limiting examples.

EXAMPLES

Example 1

*E. coli* SP1.1 cells are selected as the host cells for synthesis of aminoshikimic acid from glucose. *E. coli* SP1.1, whose formation as genomically serA-derivatives from *E. coli* strain RB791 is described in U.S. Pat. No. 6,613,552, is available as the host cell of the transformed cell lines *E. coli* SP1.1/pKD12.112 and *E. coli* SP1.1/pKD12.138, which are available under ATCC Nos. 98905 and 207055 from the American Type Culture Collection (ATCC), 10801 University Boulevard, Manassas, Va. 20110-2209. As is the case for bacteria generally, *E. coli* SP1.1 cells contain enzymes, and their encoding genes, that are capable of performing steps A, E, F, G, I, J, and K of an aminoshikimate biosynthesis pathway according to some embodiments of the present invention.

*E. coli* SP1.1 cells are transformed with plasmid pJG11.233. Plasmid pJG11.233 carries the whole yhjLKJ gene cluster from *B. subtilis*, the aminoDAHP synthase encoding gene, rifH, from *A. mediterranei*, and the aroE, serA, tktA, and $lacI^Q$ loci from *E. coli*, with the yhjLKJ, rifH, and aroE components each being under the control of the tac promoter. The resulting amplified expression of aroE-encoded shikimate dehydrogenase is intended to enhance the expected conversion of aminoDHS into aminoshikimic acid; and amplified expression of tktA is intended to increase the rate of transketolase-catalyzed ketol transfer from aminoF6P to generate iminoE4P (FIG. 1). The plasmid localized serA gene allows the serA-host strain to grow in minimal salts medium lacking L-serine supplementation.

Figure 2:
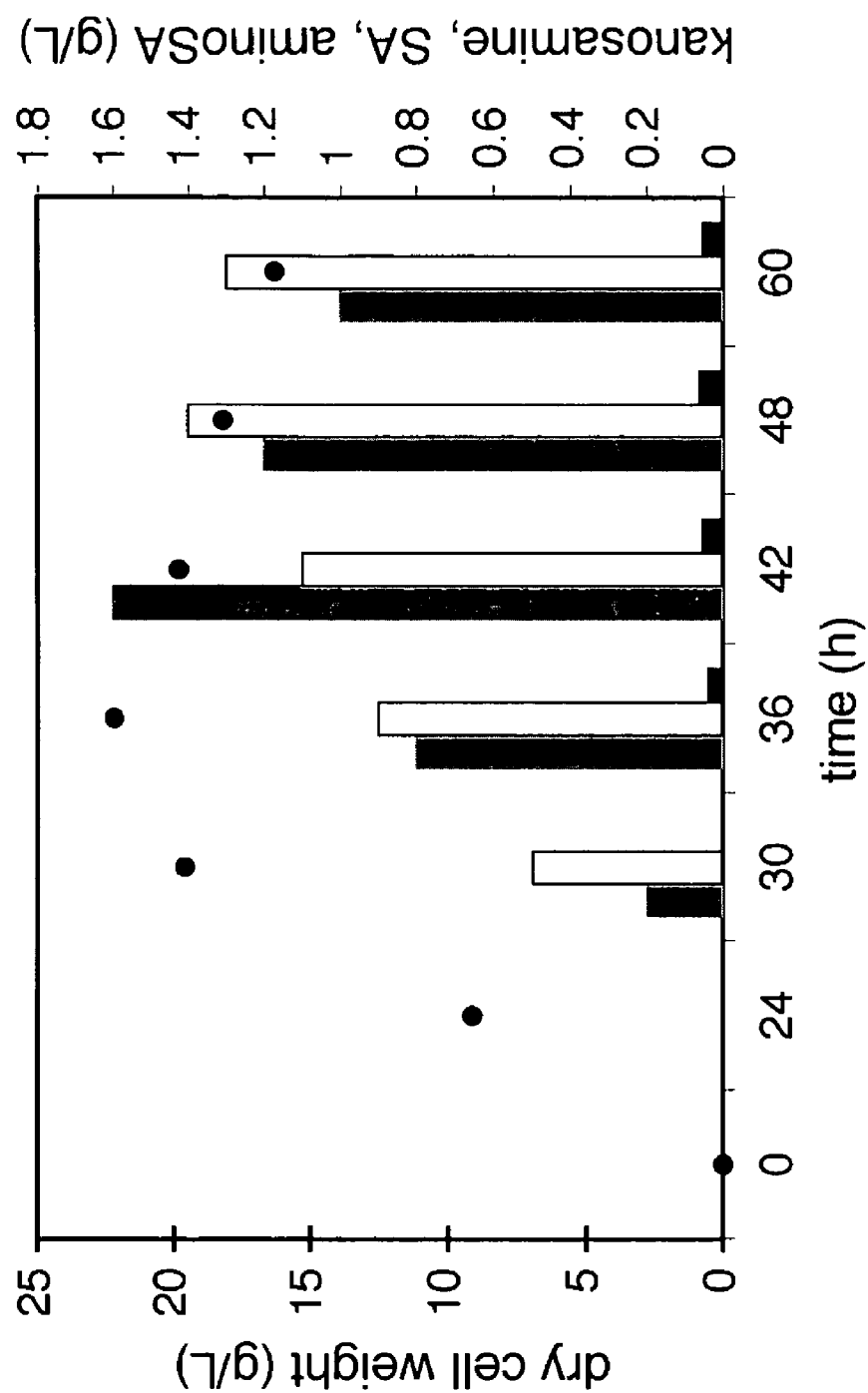
FIG. 2 illustrates results of aminoshikimic acid-synthesizing fermentations of E. coli SP1.1/pJG11.233 under fermentor-controlled conditions. Legend: kanosamine, grey columns; shikimic acid (SA), open columns; aminoshikimic acid (aminoSA), black columns; dry cell weight, closed circles.

Cultivation of *E. coli* SP1.1/pJG11.233 in minimal salts medium with 10 g/L of $(NH_4)_2SO_4$ and 1 mM IPTG for 60 h at 33° C. under fermentor-controlled conditions leads to the synthesis of 0.05 g/L of aminoshikimic acid, 1.0 g/L of kanosamine, and 1.3 g/L of shikimic acid (FIG. 2). A cation exchange resin is then used for the straightforward separation of aminoshikimic acid from kanosamine, shikimic acid, and the other components of the culture medium.

Example 2

According to one synthetic scheme (FIG. 1), kanosamine 6-phosphate could be directed into the synthesis of aminoshikimic acid without the redundant dephosphorylation and phosphorylation steps D and E if the yhjK-encoded kanosamine 6-phosphate phosphatase activity is depleted (FIG. 1). Plasmid pJG11.265 is made accordingly, which carries all the genes on plasmid pJG11.233 except for yhjK. The cultivation of *E. coli* SP1.1/pJG11.265 under conditions identical to those of Example 1, however, results in host cell death after induction with IPTG (1 mM). It appears that kanosamine-6-phosphate can inhibit glucosamine-6-phosphate synthase, which is necessary for the cell's biosynthesis of N-acetylglucosamine-containing peptidoglycan and lipid A. To partially relieve the inhibition, N-acetylglucosamine (10 mM) is added to the culture medium. After 60 h of cultivation, *E. coli* SP1.1/pJG11.265 production of 0.06 g/L of aminoshikimic acid, trace amount of kanosamine, and 3.1 g/L of shikimic acid is found.

Table 2 summarizes the results of all three fermentations.

TABLE 2

Product concentrations for catalysts when grown under equivalent culture conditions.

| Entry | Construct | aminoSA[b] (g/L) | SA[b] (g/L) | Kanosamine (g/L) |
|---|---|---|---|---|
| 1 | *E. coli* SP1.1/pJG11.233 | 0.05 | 1.3 | 1.0 |
| 2A | *E. coli* SP1.1/pJG11.265 | 0 | 0 | 0 |
| 2B[a] | *E. coli* SP1.1/pJG11.265 | 0.06 | 3.1 | Trace |

[a]N-Acetylglucosamine (10 mM) is added to the culture medium.
[b]Abbreviations: aminoSA, aminoshikimic acid; SA, shikimic acid.

As a result, the cells comprising an enzyme system according to an embodiment of the present invention are the first single-cell catalysts that are capable of biosynthesizing aminoshikimic acid directly from D-glucose in a low energy process, as the enzymatic pathways hereof represent the first low-energy aminoshikimate biosynthetic route.

The examples and other embodiments described herein are exemplary and not intended to be limiting in describing the full scope of materials, compositions and methods of this invention. The above description of various embodiments will suggest to one of ordinary skill in the art other useful embodiments. Equivalent changes, modifications and variations of specific embodiments, materials, compositions and methods may be made with substantially similar results.

What is claimed is:

1. A recombinant cell for aminoshikimate biosynthesis comprising:
   (a) a recombinant 3-keto-D-glucose-6-phosphate (3KG6P) dehydrogenase comprising the amino acid sequence of SEQ ID NO:2,
   (b) a recombinant 3-keto-D-glucose-6-phosphate (3KG6P) transaminase comprising the amino acid sequence of SEQ ID NO:4, and
   (c) a recombinant 4-amino-3,4-dideoxy-D-arabino-heptulosonic acid 7-phosphate (aminoDAHP) synthase comprising the amino acid sequence of SEQ ID NO:8, wherein the recombinant cell is capable of catalyzing conversion of glucose-6-phosphate (G6P) to 3-keto-D-glucose-6-phosphate (3KG6P), 3KG6P to kanosamine-6-phosphate (K6P), K6P to 1-imino-1-deoxy-D-erythrose-4-phosphate (iminoE4P), iminoE4P to 4-amino-3,4-dideoxy-D-arabino-heptulosonic acid 7-phosphate (aminoDAHP), and aminoDAHP to aminoshikimate.

2. The recombinant cell according to claim 1, wherein said recombinant cell comprising enzymes (a), (b) and (c) further comprises at least one of:
   (d) a phosphoglucose isomerase (Pgi) comprising the amino acid sequence of SEQ ID NO: 10;
   (e) a transketolase (TktA) comprising the amino acid sequence of SEQ ID NO: 12;
   (f) a 3-dehydroquinate (DHQ) synthase comprising the amino acid sequence of SEQ ID NO: 14, 5-amino-3-dehydroquinate (aminoDHQ) synthase, or combination thereof;
   (g) a 3-dehydroquinate (DHQ) dehydratase comprising the amino acid sequence of SEQ ID NO: 16, 5-amino-3-dehydroquinate (aminoDHQ) dehydratase, or combination thereof; or
   (h) a shikimate dehydrogenase comprising the amino acid sequence of SEQ ID NO: 18, quinate/shikimate dehydrogenase, aminoquinate/aminoshikimate dehydrogenase, or combination thereof.

3. The recombinant cell according to claim 2, wherein said recombinant cell comprising enzymes (a), (b), and (c) and at least one of (d)-(h), further comprises at least one of:
   (i) a kanosamine-6-phosphate (K6P) phosphatase comprising the amino acid sequence of SEQ ID NO: 6; or
   (j) a phosphoenolpyruvate:carbohydrate phosphotransferase system, a glucose kinase (Glk) comprising the amino acid sequence of SEQ ID NO: 20, or a kanosamine kinase.

4. The recombinant cell according to claim 2, wherein the Pgi of (d), the TktA of (e), one of the DHQ syntase or amino DHQ synthase of (f), one of the DHQ dehydratase or amino DHQ dehydratase of (g), and one of the shikimate dehydrogenase, quinate/shikimate dehydrogenase, or aminoquinate/aminoshikimate dehydrogenase of (h) are present in said recombinant cell.

5. The recombinant cell according to claim 4, wherein the recombinant cell further comprises exogenously supplied N-acetylglucosamine.

6. The recombinant cell according to claim 1, wherein said recombinant cell is selected from the group consisting of a plant cell, an animal cell, a human cell, a fungal cell, a bacterial cell, a protist cell, and an archaeal cell.

7. The recombinant cell according to claim 6, wherein said recombinant cell is selected from the group consisting of a plant cell, a fungal cell, a bacterial cell, and a protist cell.

8. The recombinant cell according to claim 7, wherein said recombinant cell is selected from the group consisting of a fungal cell and a bacterial cell.

9. The recombinant cell according to claim 8, wherein said recombinant cell is a bacterial cell.

10. The recombinant cell according to claim 9, wherein said recombinant cell is an *Escherichia coli* cell.

11. A process for producing 5-amino-5-deoxyshikimic acid (aminoshikimate) comprising the steps of:
    A) providing:
       1) a carbon source, and
       2) the recombinant cell for aminoshikimate biosynthesis according to claim 1, provided that if the carbon source does not comprise G6P then the recombinant cell is also capable of catalyzing conversion of the carbon source to glucose-6-phosphate (G6P); and
    B) contacting the carbon source with the recombinant cell under conditions in which the enzymes (a), (b), and (c)

are able to catalyze their respective reactions; whereby aminoshikimate is produced.

12. The process according to claim 11, wherein said recombinant cell comprising enzymes (a), (b) and (c) further comprises at least one of:
(d) a phosphoglucose isomerase (Pgi) comprising the amino acid sequence of SEQ ID NO: 10;
(e) a transketolase (TktA) comprising the amino acid sequence of SEQ ID NO: 12;
(f) a 3-dehydroquinate (DHQ) synthase comprising the amino acid sequence of SEQ ID NO: 14, 5-amino-3-dehydroquinate (aminoDHQ) synthase, or combination thereof;
(g) a 3-dehydroquinate (DHQ) dehydratase comprising the amino acid sequence of SEQ ID NO: 16, 5-amino-3-dehydroquinate (aminoDHQ) dehydratase, or combination thereof; or
(h) a shikimate dehydrogenase comprising the amino acid sequence of SEQ ID NO: 18, quinate/shikimate dehydrogenase, aminoquinate/aminoshikimate dehydrogenase, or combination thereof.

13. The process according to claim 12, wherein said recombinant cell comprising enzymes (a), (b), and (c) and at least one of (d)-(h), further comprises at least one of:
(i) a kanosamine-6-phosphate (K6P) phosphatase comprising the amino acid sequence of SEQ ID NO: 6; or
(j) a phosphoenolpyruvate:carbohydrate phosphotransferase system, a glucose kinase (Glk) comprising the amino acid sequence of SEQ ID NO: 20, or a kanosamine kinase.

14. The process according to claim 11, wherein said recombinant cell is selected from the group consisting of a plant cell, an animal cell, a human cell, a fungal cell, a bacterial cell, a protist cell, and an archaeal cell.

15. The process according to claim 14, wherein said recombinant cell is selected from the group consisting of a plant cell, a fungal cell, a bacterial cell, and a protist cell.

16. The process according to claim 15, wherein said recombinant cell is selected from the group consisting of a fungal cell and a bacterial cell.

17. The process according to claim 16, wherein said recombinant cell is a bacterial cell.

18. The process according to claim 17, wherein said recombinant cell is an *Escherichia coli* cell.

19. An isolated nucleic acid encoding enzymes (a), (b), and (c) of claim 1.

20. The isolated nucleic acid according to claim 19, wherein said isolated nucleic acid comprises DNA.

21. A vector comprising the isolated nucleic acid according to claim 11.

22. The vector according to claim 21, wherein said vector is any one of a plasmid, cosmid, transposon, or artificial chromosome.

23. The isolated nucleic acid according to claim 19, wherein the isolated nucleic acid comprises: an isolated nucleic acid encoding 3KG6P dehydrogenase that comprises the nucleotide sequence of SEQ ID NO:1, an isolated nucleic acid encoding 3KG6P transaminase that comprises the nucleotide sequence of SEQ ID NO:3, and an isolated nucleic acid encoding aminoDAHP synthase that comprises the nucleotide sequence of SEQ ID NO:7.

24. An isolated nucleic acid encoding:
(a) a recombinant 3-keto-D-glucose-6-phosphate (3KG6P) dehydrogenase comprising the amino acid sequence of SEQ ID NO: 2;
(b) a recombinant 3-keto-D-glucose-6-phosphate (3KG6P) transaminase comprising the amino acid sequence of SEQ ID NO: 4;
(c) a recombinant 4-amino-3,4-dideoxy-D-arabino-heptulosonic acid 7-phosphate (aminoDHP) synthase comprising the amino acid sequence of SEQ ID NO: 8;
(d) a phosphoglucose isomerase (Pgi) comprising the amino acid sequence of SEQ ID NO: 10;
(e) a transketolase (TktA) comprising the amino acid sequence of SEQ ID NO: 12;
(f) one of a 3-dehydroquinate (DHQ) synthase comprising the amino acid sequence of SEQ ID NO: 14 or a 5-amino-3-dehydroquinate (aminoDHQ) synthase;
(g) one of a 3-dehydroquinate (DHQ) dehydratase comprising the amino acid sequence of SEQ ID NO: 16, or a 5-amino-3-dehydroquinate (aminoDHQ) dehydratase; and
(h) one of a shikimate dehydrogenase comprising the amino acid sequence of SEQ ID NO: 18, a quinate/shikimate dehydrogenase, or an aminoquinate/aminoshikimate dehydrogenase.

25. An isolated nucleic acid encoding:
(a) a recombinant 3-keto-D-glucose-6-phosphate (3KG6P) dehydrogenase comprising the amino acid sequence of SEQ ID NO: 2;
(b) a recombinant 3-keto-D-glucose-6-phosphate (3KG6P) transaminase comprising the amino acid sequence of SEQ ID NO: 4;
(c) a recombinant 4-amino-3,4-dideoxy-D-arabino-heptulosonic acid 7-phosphate (aminoDHP) synthase comprising the amino acid sequence of SEQ ID NO: 8;
(d) a phosphoglucose isomerase (Pgi) comprising the amino acid sequence of SEQ ID NO: 10;
(e) a transketolase (TktA) comprising the amino acid sequence of SEQ ID NO: 12;
(f) one of a 3-dehydroquinate (DHQ) synthase comprising the amino acid sequence of SEQ ID NO: 14 or a 5-amino-3-dehydroquinate (aminoDHQ) synthase;
(g) one of a 3-dehydroquinate (DHQ) dehydratase comprising the amino acid sequence of SEQ ID NO: 16, or a 5-amino-3-dehydroquinate (aminoDHQ) dehydratase;
(h) one of a shikimate dehydrogenase comprising the amino acid sequence of SEQ ID NO: 18, a quinate/shikimate dehydrogenase, or an aminoquinate/aminoshikimate dehydrogenase;
(i) a kanosamine-6-phosphate (K6P) phosphatase comprising the amino acid sequence of SEQ ID NO: 6; and
(j) one of a phosphoenolpyruvate:carbohydrate phosphotransferase system, a glucose kinase (Glk) comprising the amino acid sequence of SEQ ID NO: 20, or a kanosamine kinase.

26. The isolated nucleic acid according to claim 24, wherein said isolated nucleic acid comprises: an isolated nucleic acid encoding 3KG6P dehydrogenase that comprises the nucleotide sequence of SEQ ID NO:1, an isolated nucleic acid encoding 3KG6P transaminase that comprises the nucleotide sequence of SEQ ID NO:3, an isolated nucleic acid encoding aminoDAHP synthase that comprises the nucleotide sequence of SEQ ID NO:7, an isolated nucleic acid encoding Pgi that comprises the nucleotide sequence of SEQ ID NO:9, an isolated nucleic acid encoding TktA that comprises the nucleotide sequence of SEQ ID NO:11, an isolated nucleic acid encoding DHQ synthase that comprises the nucleotide sequence of SEQ ID NO:13, an isolated nucleic acid encoding DHQ dehydratase that comprises the nucleotide sequence of SEQ ID NO:15, and an isolated nucleic acid encoding shikimate dehydrogenase that comprises the nucleotide sequence of SEQ ID NO:17.

27. The isolated nucleic acid according to claim 25, wherein said isolated nucleic acid comprises: an isolated nucleic acid encoding 3KG6P dehydrogenase that comprises the nucleotide sequence of SEQ ID NO:1, an isolated nucleic acid encoding 3KG6P transaminase that comprises the nucleotide sequence of SEQ ID NO:3, an isolated nucleic acid encoding aminoDAHP synthase that comprises the nucleotide sequence of SEQ ID NO:7, an isolated nucleic acid encoding Pgi that comprises the nucleotide sequence of SEQ ID NO:9, an isolated nucleic acid encoding TktA that comprises the nucleotide sequence of SEQ ID NO:11, an isolated nucleic acid encoding DHQ synthase that comprises the nucleotide sequence of SEQ ID NO:13, an isolated nucleic acid encoding DHQ dehydratase that comprises the nucleotide sequence of SEQ ID NO:15, an isolated nucleic acid encoding shikimate dehydrogenase that comprises the nucleotide sequence of SEQ ID NO:17, an isolated nucleic acid encoding K6P phosphatase that comprises the nucleotide sequence of SEQ ID NO:5, and an isolated nucleic acid encoding Glk that comprises the nucleotide sequence of SEQ ID NO:19.

28. A recombinant cell according to claim 1 comprising expressible nucleic acid encoding enzymes (a), (b), and (c) for aminoshikimate biosynthesis.

29. A process for preparing a derivative of biosynthetic aminoshikimate comprising:
(A) providing a carbon source and the recombinant cell for aminoshikimate biosynthesis according to claim 1, provided that if the carbon source does not comprise G6P then the recombinant cell is also capable of catalyzing conversion of the carbon source to glucose-6-phosphate (G6P);
(B) contacting the carbon source with the recombinant cell under conditions in which the enzymes (a), (b) and (c) are able to catalyze their respective reactions; whereby biosynthetic aminoshikimate is produced; and
(C) biosynthetically or chemosynthetically modifying the biosynthetic aminoshikimate to form a derivative thereof.

30. The process according to claim 29, wherein the modification step is a chemosynthetic modification that converts the biosynthetic aminoshikimate to an oseltamivir carboxylate.

31. The process according to claim 29, wherein the modification step is a chemosynthetic modification that converts the biosynthetic aminoshikimate to oseltamivir phosphate.

32. A process for preparing oseltamivir phosphate comprising:
(A) providing a carbon source and the recombinant cell for aminoshikimate biosynthesis according to claim 1, provided that if the carbon source does not comprise G6P then the recombinant cell is also capable of catalyzing conversion of the carbon source to glucose-6-phosphate (G6P);
(B) contacting the carbon source with the recombinant cell under conditions in which the enzymes (a), (b) and (c) are able to catalyze their respective reactions; whereby aminoshikimate is produced; and
(C) chemosynthetically converting the 1-carboxyl group in aminoshikimate to an ethyl ester group, the 3-hydroxyl group in aminoshikimate to a 3-O-(pentan-3-yl) ether group, the 4-hydroxyl group in aminoshikimate to a 4(R)-acetylamino group, and the 5-amino group in aminoshikimate to a 5(S)-amino phosphate salt or complex, thereby obtaining oseltamivir phosphate.

33. The process according to claim 29, wherein the derivative comprises any one or more of oseltamivir carboxylate, oseltamivir carboxylate salts, oseltamivir carboxylate esters, or oseltamivir carboxylate ester salts.

34. The process according to claim 33, wherein the oseltamivir carboxylate salts are selected from the group consisting of oseltamivir phosphate, oseltamivir carboxylate esters, and oseltamivir carboxylate ester salts.

35. A kit comprising an isolated, expressible nucleic acid encoding enzymes (a), (b), and (c) according to claim 1, with instructions for use thereof to produce a recombinant cell for anabolic aminoshikimate biosynthesis or to produce aminoshikimate or a derivative thereof.

36. The kit according to claim 35, wherein said kit comprises a host cell which is going to be transformed with the expressible nucleic acid.

37. The kit according to claim 35, wherein said kit contains an isolated nucleic acid encoding all enzymes of the anabolic aminoshikimate biosynthesis pathway.

38. A kit comprising the recombinant cell of claim 1, with instructions for use thereof to produce aminoshikimate or a derivative thereof.

39. The kit according to claim 38, wherein said recombinant cell is capable of expressing all enzymes of the anabolic aminoshikimate biosynthesis pathway.

* * * * *

UNITED STATES PATENT AND TRADEMARK OFFICE
CERTIFICATE OF CORRECTION

PATENT NO.          : 7,977,077 B2
APPLICATION NO.     : 11/700238
DATED               : July 12, 2011
INVENTOR(S)         : John W. Frost and Jiantao Guo It is certified that error appears in the above-identified patent and that said Letters Patent is hereby corrected as shown below:

In the Specifications

Column 1, Line 14, delete "Certain aspects, of the present inventions were developed with support under grant 5R01GM065541-04 from the National Institutes of Health. The U.S. Government may have rights in certain of these inventions." and insert therefor: -- This invention was made with government support under R01 GM065541 awarded by the National Institutes of Health. The government has certain rights in the invention. --

Signed and Sealed this
Twenty-fifth Day of March, 2014

Michelle K. Lee
*Deputy Director of the United States Patent and Trademark Office*